(12) United States Patent
Chiquet-Ehrismann et al.

(10) Patent No.: US 7,683,159 B2
(45) Date of Patent: Mar. 23, 2010

(54) TENASCIN-W COMPOSITIONS AND USES THEREOF

(75) Inventors: Ruth Chiquet-Ehrismann, Reinach (CH); Arnaud Scherberich, Riedisheim (FR)

(73) Assignee: Novartis Forschungsstiftung Zweignlederlassung Friedrich Miescher Institute for Biomedical Research, Basel (CH)

( * ) Notice: Subject to any disclaimer, the term of this patent is extended or adjusted under 35 U.S.C. 154(b) by 640 days.

(21) Appl. No.: 10/509,009

(22) PCT Filed: Mar. 26, 2003

(86) PCT No.: PCT/EP03/03150

§ 371 (c)(1),
(2), (4) Date: May 3, 2005

(87) PCT Pub. No.: WO03/080663

PCT Pub. Date: Oct. 2, 2003

(65) Prior Publication Data

US 2005/0202430 A1    Sep. 15, 2005

(30) Foreign Application Priority Data

Mar. 27, 2002    (GB) ................. 0207224.7

(51) Int. Cl.
*C07K 16/00* (2006.01)
*A61K 39/395* (2006.01)
(52) U.S. Cl. ................. 530/387.1; 424/130.1
(58) Field of Classification Search ........ None
See application file for complete search history.

(56) References Cited

U.S. PATENT DOCUMENTS

| 6,124,260 A | 9/2000 | Sharifi et al. |
| 2002/0151009 A1* | 10/2002 | Ni et al. ............... 435/183 |
| 2002/0182586 A1* | 12/2002 | Morris et al. ........... 435/4 |
| 2003/0022255 A1 | 1/2003 | Morris et al. |

FOREIGN PATENT DOCUMENTS

| WO | WO 9204464 | 3/1992 |
| WO | WO 9421293 | 9/1994 |

OTHER PUBLICATIONS

Bachman, M.F., Wolint, P., Schwartz, K. and Oxenius, A. Recall proliferation potential of memory CD8+ T cells and antiviral protection. Journal of Immunology, 2005. vol. 175, pp. 4677-4685.*
Efferson, C.L., Kawano, K., Tsuda, N., Palese, P., Garcia-Sastre, A., and Ioannides, C.G. Stimulation of human T cells by an influenza A vector expressing a CTL epitope from the HER-2/neu protooncogene results in higher numbers of antigen-specific TCRhi cells than stimulation with peptide. Anticancer Research, 2005. vol. 25, pp. 715-724.*
Wheeler, C.M. Preventive vaccines for cervical cancer. Salud Publica de Mexico, 1997. vol. 39 No. 4.*
Weber, Montag, Schachner, and Bernhardt. Zebrafish tenascin-W, a new member of the tenascin family. Journal of Neurobiology, 1998. vol. 35, pp. 1-16.*
Campbell. Monoclonal Antibody Technology. Elsevier Science Publishers, 1984. pp. 1-32.*
Arakawa, et al. "*Mus musculus* 16 Days Embryo Head cDNA", Database EMBL Online; Accession No. BB648643—XP002250801 (2001).
Zhao, et al. "RPCI-24-112D17.TV RPCI-24 *Mus musculus* Genomic Clone RPCI-24-112D17", Database EMBL Online, Accession No. AZ748340 XP002250802 (2001).
Rhodes, S., "Novel Human MRNA from Chromosome 1, Similar to Tenanscin-R", Database EMBL Online, Accession No. AL049689 (1999).
Abe, et al., "Purification of Primordial Germ Cells from TNAP Bgeo Mouse Embryos Using FACS-gal", Develop. Biol., vol. 180, pp. 468-472 (1996).
Akamatsu, et al., "Suppression of Transformed Phenotypes of Human Fibrosarcoma Cells by Overexpresion of Recombinant Fibronectin", Cancer Res., vol. 56, pp. 4541-4546 (1996).
Bloom, et al., "Fibronectin Regulates Assembly of Actin Filaments and Focal Contacts in Cultured Cells Via the Heparin-binding Site in Repeat III 13", Mol. Biol. of the Cell, vol. 10, pp. 1521-1536 (1999).
Boudreau, et al., "Extracellular Matrix Signaling: Integration of Form and Function in Normal and Malignant Cells", Current Opin. in Cell Biol., vol. 10, pp. 640-646 (1998).
Bourdon, et al., "Human Glioma-mesenchymal Extracellular Matrix Antigen Defined by Monoclonal Antibody", Cancer Res., vol. 43, pp. 2796-2805 (1983).
Burch, et al., "Tenascin-X Deficiency Is Associated with Ehlers-Danlos Syndrome", Nature Gen., vol. 17, pp. 104-108 (1997).
Chiquet, et al., "Chick Myotendinous Antigen II. A Novel Extracellular Glycoprotein Complex Consisting of Large Disulfide-linked Subunits", J. of Cell Biol., vol. 98, pp. 1937-1946 (1984).
Chiquet, et al., "Chick Myotendinous Antigen I. A Monoclonal Antibody as a Marker for Tendon and Muscle Morphogenesis", J. of Cell Biol., vol. 98, pp. 1926-1936 (1984).
Chiquet-Ehrismann, "Tenascins, A Growing Family of Extracellular Matrix Proteins", Experienta, vol. 51, pp. 853-862 (1995).
Chiquet-Ehrismann, "Tenascin and Other Adhesion-modulating Proteins in Cancer", Cancer Biol., vol. 4, pp. 301-310 (1993).

(Continued)

*Primary Examiner*—David J. Blanchard
*Assistant Examiner*—Anne M. Gussow
(74) *Attorney, Agent, or Firm*—Hoxie & Associates LLC

(57) ABSTRACT

Tenascin-W, an extracellular matrix molecule that is specifically expressed in metastatic tumours is provided. A system comprising a sample expressing tenascin-W is used as an in vitro method for screening possible anti-tumour agents or for agents that promote osteogenesis.

7 Claims, No Drawings

OTHER PUBLICATIONS

Chiquet-Ehrismann, et al. "Tenascin: An Extracellular Matrix Protein Involved in Tissue Interactions During Fetal Development and Oncogenesis", Cell, vol. 47, pp. 131-139 (1986).

Chiquet-Ehrismann, et al., "Tenascin Interferes with Fibronectin Action", Cell, vol. 53, pp. 383-390 (1988).

Denda, et al. Utilization of a Soluble Integrin-alkaline Phosphatase Chimera to Characterize Integrin a8/B1 Receptor Interactions with Tenasin: Murine a8/B1 Binds to the RGD Site in Tenascin-C Fragments, but Not to Native Tenascin-C, Biochem., vol. 37, pp. 5464-5474 (1998).

Erickson, et al., "A Six-armed Oligomer Isolated from Cell Surface Fibronectin Preparations", Nature, vol. 311, pp. 267-269 (1984).

Huse, et al., "Generation of a Large Combinatorial Library of the Immunoglobulin Repertoire in Phage Lambda", Science, vol. 246, pp. 1275-1281 (1989).

Kohfeldt, et al., "Properties of the Extracellular Calcium Binding Module of the Proteoglycan Testican", FEBS, vol. 414, pp. 557-561 (1997).

Kohler, et al., "Continuous Cultures of Fused Cells Secreting Anitbody of Predefined Specificity", Nature, vol. 256, pp. 495-497 (1975).

Koyama, et al., "Expression of Syndecan-3 and Tenascin-C: Possible Involvement in Periosteum Development", J. of Ortho. Res., vol. 14, pp. 403-412 (1996).

Latijnhouwers, et al., "Tenascin Expression During Wound Healing in Human Skin", J. of Path., vol. 178, pp. 30-35 (1996).

Li, et al., "Expression of Stromelysin-1 and TIMP-1 in the Involuting Mammary Gland and in Early Invasive Tumors of Mouse", Int. J. Cancer, vol. 59, pp. 560-568 (1994).

Munarini, et al., "Altered Mammary Epithelial Development, Pattern Formation and Involution in Transgenic Mice Expressing the EphB4 Receptor Tyrosine Kinase", J. of Cell Science, vol. 115, pp. 25-37 (2002).

Giancotti, et al. "Elevated Levels of the a5B1 Fibronectin Receptor Suppress the Transformed Phenotype of Chinese Hamster Ovary Cells", vol. 60, pp. 849-859 (1990).

Hagios, et al., "Tenascin-Y: A Protein of Novel Domain Structure Is Secreted by Differentiated Fibroblasts of Muscle Connective Tissue", J. of Cell Biol., vol. 134, pp. 1499-1512 (1996).

Hall, et al., "Divid, Accumulate, Differentiate: Cell Condensation in Skeletal Development Revisited", Int. J. Dev. Biol., vol. 39, pp. 881-893 (1995).

Ward, et al., "Binding Activities of a Repertoire of Single Immunoglobulin Variable Domains Secreted from *Escherichia coli*", Nature, vol. 341, pp. 544-546 (1989).

Weber, et al., "Zebrafish Tenascin-W, a New Member of the Tenascin Family", Swiss Fed. Inst. Of Tech., Zurich, pp. 1-16 (1997).

Yokosaki, et al., "Differential Effects of the Integrins a9B1, avB3, and avB6 on Cell Proliferative Responses to Tenascin", J. of Biol. Chem., vol. 271, pp. 24144-24150 (1996).

Yokosaki, et al., "Identification of the Ligand Binding Site for the Integrin a9B1 in the Third Fibronectin Type III Repeat of Tenascin-C", J. of Biol. Chem., vol. 273, pp. 11423-11428 (1998).

Neidhardt, et al. "Tenascin-N: Characterization of a Novel Member of the Tenascin Family that Mediates Neurite Repulsion from Hippocampal Explants", Mol. and Cell. Neuro., vol. 23, pp. 193-209 (2003)*.

Neidhardt, et al. "*Mus musculus* Tenascin-N (tnn) mRNA", Database EMBL Online, Database Accession No. AF455756 (2002)*.

Adachi, et al., "*Mus musculus* 16 Days Embryo Head cDNA", Database EMBL online, Database Accession No. AK048033 (2002)*.

Philipp, et al., "Zebrafish Tenascin-W, a New Member of the Tenascin Family", J. of Neurobiology, vol. 35, pp. 1-16 (1998)*.

Mackie, et al., "Induction of Tenascin In Wound Healing", J. Cell. Biol., vol. 107, pp. 2757-2567 (1988) ([To Be Provided].

Hauptmann, et al. "Extracellular Matrix Proteins in Colorectal Carcinomas", Lab. Invest., vol. 73 (1995).

Jones, et al., "The Tenascin Family of ECM Glycoproteins: Structure, Function, and Regulation During Embryonic Development and Tissue Remodeling", Dev. Dynamics, vol. 218 (2000).

Norderhaug, et al., "Versatile Vectors for Transient and Stable Expression of Recombinant Antibody Molecules in Mammalian Cells", J. of Imm. Meth., vol. 204 (1997).

Pesheva, et al., "Tenascin-R as a Regulator of CNS Glial Cell Function", Prog. in Brain Res., vol. 132 (2001).

Raouf, et al., "Discovery of Osteoblast-associated Genes Using cDNA Microarrays", Bone, vol. 30 (2002).

Riva, et al, "Loco-regional Radioimmunotherapy of High-grade Malignant Gliomas Using Specific Monoclonal Antibodies Labeled with 90Y: A Phase I Study", Clin. Can. Res., vol. 5 (1999).

Riva, et al., "131I Radioconjugated Antibodies for the Locoregional Radioimmunotherapy of High-grade Malignant Glioma", Acta Onc., vol. 38 (1999).

Ruoslahti, "Fibronectin and Its Integrin Receptors in Cancer", Advances in Cancer Res. (1999).

Schenk, et al., "Tenascin-C in Serum: A Questionable Tumor Marker", Int. J. Cancer, vol. 61 (1995).

Zalutsky, et al., "High-level Production of a-Particle-Emitting 211 At and Preparation of 211 At-Labeled Antibodies for Clinical Use", J. of Nuc. Med., vol. 42 (2001).

Reardon, David A. et al., Phase II Trial of Murine [131]I-Labeled Antitenascin Monoclonal Antibody 81C6 Administered Into Surgically Created Resection Cavities of Patients With Newly Diagnosed Malignant Gliomas; Journal of Clinical Oncology, vol. 20; No. 5; pp. 1389-1397; Mar. 1, 2002.

Amino Acid, Wikipedia Encyclopedia, pp. 1-9.

Leucine, Wikipedia Encyclopedia, pp. 1-2.

Proline, Wikipedia Encyclopedia, pp. 1-2.

Proteinogenic Amino Acid, Wikipedia Encyclopedia, pp. 1-6.

Sickle-cell Disease, Wikipedia Encyclopedia, pp. 1-6.

* cited by examiner

TENASCIN-W COMPOSITIONS AND USES THEREOF

CROSS REFERENCE TO RELATED APPLICATIONS

This application is a U.S. filing under 35 U.S.C. 371 of PCT/EP2003/03150 filed on Mar. 26, 2003, which claims the benefit of GB 0207224.7 filed on Mar. 27, 2002, the contents of each of which are incorporated herein by reference.

The present invention relates to polypeptides specifically expressed in tumours, to active agents having anti-tumour and/or anti-tumourigenic activity and to agents effective in improving conditions dependent on stem cell differentiation, in particular osteoblast formation, such as in osteogenesis, to pharmaceutical compositions of these agents and to the pharmaceutical uses of such agents and compositions. The invention also relates to in vitro methods of screening agents for anti-tumour and/or anti-tumourigenic activity as well as for agents effective in promoting stem cell differentiation.

The adherence of cells to each other and to the extracelluar matrix (ECM) as well as the cellular signals transduced as a consequence of such binding are of fundamental importance to the development and maintenance of body form and function. The ECM has an important regulatory function in tissue homeostasis and, together with oncogenes and tumour suppressor genes is critically involved in tumourigenesis (reviewed in Boudreau, N. & Bissell, M. J. (1998) Curr Opin Cell Biol 10: 640-646 and Ruoslahti, E. (1999) Adv Cancer Res 76:1-20).

In the more affluent countries of the world cancer is the cause of death of roughly one person in five with the five most common cancers being those of the lung, stomach, breast, colon/rectum and the uterine cervix. Tumors of this type often metastasize through lymphatic and vascular channels. Cancer is not fatal in every case and only about half the number of people who develop cancer die of it. The problem facing cancer patients and their physicians is that seeking to cure cancer is like trying to get rid of weeds.

One way to treat cancer effectively is to get an early diagnosis. Most cancers are not extensively vascularized (and therefore not invasive) during the early stages of development. The transition to a highly vascularized, invasive and ultimately metastatic cancer which spreads throughout the body commonly takes ten years or longer. If the cancer is detected prior to invasion, surgical removal of the cancerous tissue is an effective cure. However, cancer is often detected only upon manifestation of clinical symptoms. Generally, such symptoms are present only when the disease is well established, often after metastasis has occurred, and the prognosis for the patient is poor, even after surgical resection of the cancerous tissue. Early detection of cancer therefore is important in that detection may significantly reduce morbidity. A reliable, non-invasive, and accurate technique for diagnosing cancer at an early stage would help save many lives.

Cancer cells can be removed surgically or destroyed with toxic compounds or with radiation but it is very hard to eliminate all of the cancerous cells. A general goal is therefore to find better ways of selectively killing cancer cells whilst leaving normal cells of the body unaffected. Part of that effort involves identifying new anti-cancer agents.

Apart from tumorgenesis, the ECM has an important regulatory function in tissue homeostasis and in the development and maintenance of body form and function, e.g. in the development or remodeling of skeleton or in bone morphogenesis. Bone marrow has stem cells with osteogenic potential and is made up of determined osteogenic precursor cells that are committed to osteogenesis and of inducible osteogenic precursor cells. Determined osteogenic precursor cells can differentiate into bone without an exogenous signal. Inducible osteogenic precursor cells require a molecular signal for initiating the differentiation program, e.g. induction by binding to extracellular matrix.

A number of molecules mediating cell adhesion have been identified and characterized at the molecular level both in vertebrates and invertebrates. Tenascins are a family of large multimeric extracellular matrix proteins, each having homologous subunits built from variable numbers of repeated domains. These include heptad repeats, epidermal growth factor (EGF)-like repeats, fibronectin type III domains and a C-terminal globular domain which is also found in fibrinogens. Tenascin-C was the first member of the family to be discovered, in one instance as a myotendinous antigen (Chiquet, M. & Fambrough, D. M., 1984) J Cell Biol 98(6):1937-1946) and in another, as a protein enriched in the stroma of gliomas (Bourdon, M. A. et al (1983) Cancer Res 43(6):2796-2805, reflecting the major sites of tenascin-C expression, namely in tendons and ligaments and the extracellular matrix of tumor stroma. A further instance of the discovery of tenascin-C (also termed hexabrachion) reflects its interaction with fibronectin (Erickson, H. P. et al. (1984) Nature 311(5983): 267-9). Enforced interaction of tumour cells with fibronectin can block proliferation in cell culture and can decrease tumour growth in nude mice (Akamatsu H. et al (1996) Cancer Res 56: 4541-4546 and Giancotti, F. G & Ruoslahti E. (1990) Cell 60: 849-859). Tenascin-C was shown to disrupt the interaction of cells with fibronectin and in this manner may enhance tumour cell proliferation. Chiquet-Ehrismann, R. et al (1988) Cell 53: 383-390 were the first to show that tenascin-C blinds to fibronectin, blocks cell attachment to fibronectin and increases proliferation of rat breast adenocarcinoma cells (Chiquet-Ehrismann, R. et al (1986) Cell 47: 131-139).

Tenascin-C is present in a large number of developing tissues including the nervous system. Although abundant in mature ligaments and tendons, it is absent from skeletal and heart muscle, unless the muscle has been injured. Tenascin-C expression is elevated in essentially all carcinomas as well as in many other types of tumors (for review see Chiquet-Ehrismann, R. (1993) Semin Cancer Biol 4(5):301-10). Furthermore, tenascin-C is upregulated in wound healing (Latijnhouwers, M. A. et al. (1996) J. Pathol 178(1):30-5), during skeletogenesis (Koyama, E. et al (1996) J Orthop Res. 14(3): 403412 and Hall, B. K. & Miyake, T. (1995) Int J Dev Biol. 39(6):881-893) as well as in many diseases involving infections and inflammation (Schenk, S. et al. (1995) Int J Cancer 61(4):443-9).

Each tenascin family member exhibits a specific gene expression pattern during embryogenesis and in the adult (for review see Chiquet-Ehrismann, R. (1995) Experientia 51(9-10):853-62) suggesting specific roles for each member. Tenascin-R is an extracellular matrix component of the nervous system found mainly in brain tissue (Pasheva, P. et al. (2001) Prog Brain Res. 132:103-14. Review), whereas tenascin-X is prominently expressed in muscle and skin connective tissue. In one patient, tenascin-X deficiency has been reported to result in an Ehler's Danlos phenotype (Burch, G. H. et al. (1997) Nat Genet 17(1):104-8).

To date there is only one report on tenascin-W available in the literature. (Weber, P. et al. (1998) J Neurobiol 35(1):1-16). In this study, a cDNA encoding tenascin-W was isolated from a 20-28 h postfertilization zebrafish cDNA library on the basis of the conserved epidermal growth factor-like domains found in all tenascin molecules. The expression pattern of tenascin-W transcripts was studied in the developing zebrafish by in situ hybridisation. It was found to be present in neural crest and sclerotome cells and the developing skeleton. Genebank sequence AJ001423 provides a zebrafish tenascin-W, and AL049689 provides a "novel human mRNA from chromosome 1, similar to Tenascin-R", whose function is not known.

The present invention provides a composition comprising an isolated nucleic acid molecule having a nucleotide sequence selected from the group consisting of:
  (a) a nucleotide sequence as set forth in SEQ ID NO:1;
  (b) a nucleotide sequence encoding the amino acid sequence shown in SEQ ID NO:2;
  (c) a nucleotide sequence with at least 85% identity to the sequence of (a) or (b);
  (d) a subsequence of more than 50 consecutive nucleotides of a sequence of (a), (b) or (c); and
  (e) a nucleotide sequence complementary to any of the nucleotide sequences or subsequence in (a), (b), (c) or (d).

In one aspect of the invention, the isolated nucleic acid molecule having a nucleotide sequence preferably exhibits at least 85% identity to the sequence of (a), more preferably encoding a variant of the amino acid sequence shown in SEQ ID NO:2, such as a variant comprising an amino acid deletion, addition (e.g. fusion proteins) or substitution of the amino acid sequence shown in SEQ ID NO:2. Preferably, the variant comprises a conservative substitution of at least one amino acid in said amino acid sequence in SEQ ID NO:2, more preferably the variant has stem cell differentiation inducing activity, in particular an activity that induces osteoblast development from stem cells. Most preferred is when the isolated nucleic acid molecule encodes a protein with the amino acid sequence shown in SEQ ID NO:2.

The nucleic acid molecule can be an antisense molecule, in which case it might be desirable to have nucleotide residues that are resistant to nuclease degradation substituting some or all of the ribo- or deoxyribonucleotides.

Also provided are nucleic acid vectors comprising the nucleic acid molecules of the invention, as well as host cells comprising the vectors or nucleic acids, and transgenic, knockout or genetically modified animals (other than humans, in particular mice), comprising manipulated nucleic acids of the invention or absence the endogenous sequence.

The invention also provides a composition comprising an isolated polypeptide having an amino acid sequence selected from the group consisting of:
  (a) an amino acid sequence as set forth in SEQ ID NO. 2; and
  (b) an amino acid sequence with at least 85% identity to the sequence of (a); and
  (c) a subsequence of at least 30 consecutive amino acids of the sequence of (a) or (b), with the proviso that said subsequence does not fall within amino acid nos. 1102 and 1152 of SEQ ID NO:2.

Preferably, the amino acid sequence in (b) comprises a conservative substitution of at least one amino acid of the amino acid sequence of SEQ ID NO:2. More preferably, the polypeptide or fragment has stein cell differentiation inducing activity, as described above. Useful fragments may exhibit an epitope recognized by polyclonal antibodies raised against the polypeptide having the amino acid sequence shown in SEQ ID NO:2, for example. A particularly preferred polypeptide is that encoded by the amino acid sequence shown in SEQ ID NO:2.

Also provided are antibodies that are specifically reactive against the polypeptides of the invention.

In another aspect of the invention, a composition comprising an isolated nucleic acid molecule having a nucleotide sequence selected from the group consisting of:
  (a) a nucleotide sequence as set forth in SEQ ID No. 1 or SEQ ID No. 3;
  (b) a nucleotide sequence encoding the amino acid sequence shown in SEQ ID NO:2 or SEQ ID NO:4;
  (c) a nucleotide sequence with at least 35% identity to any one of the sequences of (a) or (b), preferably (a),
  (d) a subsequence of a least 15 consecutive nucleotides of the sequence of (a), (b) or (c); and
  (e) a nucleotide sequence complementary to (a), (b), (c), or (d), and a pharmaceutically acceptable excipient, diluent or carrier.

In one embodiment, the nucleic acid molecule preferably encodes a protein having stem cell differentiation inducing activity. In another embodiment, the nucleic acid molecule has a subsequence that is antisense to SEQ ID NO:1 or SEQ ID NO:3, wherein the nucleic acid molecule may comprise nucleotide residues that are resistant to nuclease degradation. In another embodiment, the isolated nucleic acid molecule encodes the amino acid sequence shown in SEQ ID NO:2 or SEQ ID NO:4. In yet another embodiment, the nucleic acid molecule has a subsequence selected from the group consisting of nucleotides 2380-3171 of SEQ ID NO:1, nucleotides 2371-3162 of SEQ ID NO:3, a complement of nucleotides 2880-3171 of SEQ ID NO:1, and a complement of nucleotides 2371-3162 of SEQ ID NO:2, or an RNA equivalent thereof Thus, also provided are nucleic acid compositions as described above for use as a pharmaceutical, as well as the use of such compositions for the manufacture of a medicament for the prophylaxis or treatment of cancer or bone pathologies.

Also provided are compositions comprising tenascin-W, preferably recombinant tenascin-W, and a pharmaceutically acceptable excipient, diluent or carrier. In preferred embodiments, the tenascin-W is a polypeptide having an amino acid sequence selected from the group consisting of:
  (a) an amino acid sequence as set forth in SEQ ID No. 2 or 4;
  (b) an amino acid sequence with at least 35% identity to the sequence of (a); and
  (c) a subsequence of at least 30 consecutive amino acids of the sequence of (a) or (b).

Preferably, the polypeptide has stem cell differentiation inducing activity as described above. More preferably, the polypeptide is encoded by the amino acid sequence shown in SEQ ID NO:4.

Thus, also provided is the use of tenascin-W for the treatment or prophylactic treatment of any disease or condition requiring increased tenascin-W levels, e.g. thrombosis, wound healing or atherosclerosis, as well as a condition ameliorated by the promotion of osteogenesis, e.g. bone healing, osteoporosis, as well as the use of tenascin-W as a stem cell marker.

Also provided are antibodies that specifically recognizes tenascin W for use as a pharmaceutical, as well as for the manufacture of a medicament, for the prophylaxis or treatment of cancer (e.g., glioblastoma, prostate, lung, colorectal, osteo- or breast carcinoma), including metastatic cancer, or for the prophylaxis or treatment of any disease or condition involving tenascin-W, e.g. excessive bone growth.

The present invention also provides methods for identifying agents for the prevention or the prophylactic treatment of tumourigenesis or the treatment or prophylactic treatment of tumours or cancer, or the treatment or prophylactic treatment of any disease or condition involving tenascin-W, e.g. a condition ameliorated by the promotion or inhibition of osteogenesis, comprising contacting a test compound with a tenascin-W expressing cell sample and then measuring a change in one or more of:
(a) cell proliferation e.g. cell progression entering S-phase of the cell cycle;
(b) DNA synthesis;
(c) cell adhesion;
(d) cell spreading;
(e) focal adhesion and actin stress fibre formation on fibronectin; and
(f) cell binding to extracellular matrix (ECM)
relative to when said test compound is absent.

Optionally, the method further comprises measuring, a change in tenascin-W expression relative to when the test compound is absent. The tenascin-W may have any one-or more of the features described above. A particularly preferred assay is carried out in the form of an enzyme linked immunosorbent assay (ELISA).

Also provided is a method for identifying modulators of tenascin W function, comprising:
(a) contacting a test compound with tenascin W and/or alpha8 betal integrin, and
(b) measuring the binding of the test compound to tenascin-W and/or alpha8 betal integrin, or
(c) measuring a disruption of binding of tenascin-W to alpha8 beta1 integrin, relative to when the test compound is absent.

Optionally the method further comprises measuring the binding of a control compound to tenascin-W. In one embodiment, the tenascin-W is attached to a solid surface, for example using an antibody reactive against tenascin-W. The binding can be conveniently detected using an antibody labelled with a fluorescent label, a fluorescence quencher, a radioactive label, a scintillant or an enzyme. Alternatively, the binding is detected by measuring the adhesion of alpha8 betal to the immobilized tenascin-W (as described in example 8) or vice versa. A decrease in binding of tenascin-W to alpha8 betal integrin is indicative of an inhibitor of the tenascin-W to alpha8 betal integrin interaction (and therefore an inhibitor of tenascin W function). An increase in binding of tenascin-W to alpha8 betal integrin in the presence of a test compound is indicative of a potential agent that activates alpha8 betal integrin, thereby acting as an agonist of tenascin-W function.

Thus also provided, are agents for the prevention or the prophylactic treatment of tumourigenesis or the diagnosis or the treatment or prophylactic treatment of tumours, or the treatment or prophylactic treatment of any disease or condition involving tenascin-W, e.g. a condition ameliorated by the promotion of osteogenesis, identified by a screening method of the invention.

Also provided are methods of diagnosing or prognosing cancer comprising:
(a) analysing a sample obtained from an individual for the presence of tenascin-W; and
(b) correlating the presence of tenascin-W with an unfavourable prognosis or diagnosis.

Optionally, the method may further comprise correlating in an increase in (elevated level of) tenascin-W in the sample relative to healthy tissue with an unfavourable prognosis or diagnosis. Tenascin-W can be conveniently detected using an antibody specific for tenascin-W or alternatively tenascin-w can be detected at the transcript level using techniques well known in the art, such as a polymerase chain reaction (e.g., RT-PCR) The method may also include the additional use of controls.

The sample can be blood serum from an individual, for example. The method may also further comprise propagating cells in a sample in cell culture. In one embodiment, the method further comprises analysing the sample for the presence of alpha 8 integrin, the presence of alpha 8 integrin correlating with an unfavourable prognosis or diagnosis.

The present inventors have investigated extracellular matrix molecules, their expression during development, cell adhesion and proliferation of tumour cells and have characterized a novel member of the mammalian tenascin family. Prior to the present invention, no tenascin-W had been identified from a mammalian source and its function was not previously known. The present inventors have identified and characterized the complete cDNA sequence encoding the mouse and human tenascin-W. Antisera were prepared against a fragment of tenascin-W, which detect tenascin W in tumour stroma, in the periosteum and in liver tissue, and cross react with tenascin W from several mammalian species. In particular, the inventors have discovered that tenascin-W is specifically expressed in metastatic tumour cells as well as in the periosteum, the stem cell compartment for osteogenesis.

Thus, in one aspect, the present invention provides a composition comprising an isolated nucleic acid molecule having a nucleotide sequence selected from the group consisting of:
(a) a nucleotide sequence as set forth in SEQ ID NO:1;
(b) a nucleotide sequence encoding the amino acid sequence shown in SEQ ID NO:2;
(c) a nucleotide sequence with at least 85% identity to the sequence of (a) or (b);
(d) a subsequence of more than 50, 75, 100, 200 or more consecutive nucleotides of a sequence of (a), (b) or (c); and
(e) a nucleotide sequence complementary to any of the nucleotide sequences or subsequence in (a), (b), (c) or (d).

The compositions include various types of nucleic acid, including genomic DNA, cDNA and mRNA, for example. In one aspect of the invention, the isolated nucleic acid molecule having a nucleotide sequence preferably exhibits at least 85% identity, more preferably 90% identity, most preferably 95, 98 or 100% identity to the sequence of (a) (SEQ ID NO:1). Also encompassed are nucleic acids that encode polypeptides having the amino acid sequence shown in SEQ ID NO:2, or variants thereof such as a variant comprising an amino acid deletion, addition (e.g. fusion proteins) or substitution relative to the amino acid sequence shown in SEQ ID NO:2. The various nucleic acids that can encode these polypeptides therefore may differ because of the degeneracy of the genetic code, in that most amino acids are encoded by more than one triplet codon. The identity of such codons is well known in this art, and this information can be used for the construction of the nucleic acids within the scope of the invention. Variants differ from wild-type protein in having one or more amino acid substitutions that either enhance, add, or diminish a biological activity of the wild-type protein. Once the amino acid change is selected, a nucleic acid encoding that variant is constructed according to methods well known in the art.

Preferably, the variant comprises a conservative substitution of at least one amino acid in said amino acid sequence in SEQ ID: NO:2. The variant will typically exhibit a biological function of the polypeptide as set forth in SEQ ID NO:2, that is, stem cell differentiation inducing activity, in particular an activity that induces osteoblast development from stem cells, or binding to an antibody that specifically recognizes Tenascin-W. To maintain biological activity, only conservative substitutions are therefore preferred as is well known in the art.

Most preferred is when the isolated nucleic acid molecule encodes a protein with the amino acid sequence shown in SEQ ID NO:2.

The nucleic acid molecule can be an antisense molecule, in which case it might be desirable to have nucleotide residues that are resistant to nuclease degradation substituting some or all of the ribo-or deoxyribonucleotides. Such nucleotide residues resistant to nucleases are well known in the art and can be easily synthesized by chemical means.

Also provided are nucleic acid vectors conprising the nucleic acid molecules of the invention, as well as host cells comprising the vectors or nucleic acids, and transgenic, knockout or genetically modified animals (other than humans, in particular mice), comprising manipulated nucleic acids of the invention or absent the endogenous sequence.

The invention also provides a composition comprising an isolated polypeptide having an amino acid sequence selected from the group consisting of:
  (a) an amino acid sequence as set forth in SEQ ID NO:2;
  (b) an amino acid sequence with at least 85% identity, preferably 90, 95, 98 or 100% identity to the sequence of (a); and
  (c) a subsequence of at least 30, 40, 50, 75, 100 or more consecutive amino acids of the sequence of (a) or (b), with the proviso that said subsequence does not fail within amino acid nos. 1102 and 1152 of SEQ ID NO:2.

Preferably, the amino acid sequence in (b) comprises a conservative substitution of at least one amino acid of the amino acid sequence of SEQ ID: NO:2. More preferably, the polypeptide or fragment has stem cell differentiation inducing activity, as described above. Useful fragments may exhibit an epitope recognized by polyclonal antibodies raised against the polypeptide having the amino acid sequence shown in SEQ ID NO:2, for example. A particularly preferred polypeptide is that encoded by the amino acid sequence shown in SEQ ID NO:2, derived from mouse tissue.

Therefore, also included within the invention are variants and derivatives of the polypeptide described by SEQ ID NO:2 or fragment thereof, whether produced by recombinant means or synthetic means or isolated from naturally occurring sources. For example, peptides having modified amino acids/peptide linkages, and peptides containing non-naturally occurring amino acids and/or cyclic peptides, which may have improved properties such as stability or activity are included. In addition the peptides of the invention may be in the form or a fusion with another protein, for example, tags for the targeted delivery or detection, or purification of the polypeptide (including fragments thereof.

A "variant" in terms of amino acid sequence defines an amino acid sequence that differs by one or more amino acids from another, usually related amino acid sequence. The variant may have "conservative" changes, wherein a substituted amino acid has similar structural or chemical properties (e.g. replacement of leucine with isoleucine). Less likely, a variant may have "non-conservative" changes, e.g. replacement of a glycine with a tryptophan. Similar minor variations may also include amino acid deletions or insertions (i.e. additions), or both. Guidance in determining which and how many amino acid residues may be substituted, inserted or deleted without abolishing activity (e.g., anti-cancer activity, osteoblast promoting activity, antigenic activity) may be found using computer programs well known in the art. Variants of the polypeptides of the invention include all forms of mutant variants, for example wherein at least one amino acid is deleted or substituted. Any changes involving substitution of amino acids are preferably neutral or conservative substitutions. Other variants include proteins or polypeptides comprising at least one additional amino acid in the sequence, and/or further comprising an additional amino acid sequence or domain, such as fusion proteins, as is well known in the art.

Further variants of the polypeptides of the invention include those wherein at least one of the amino acids in the sequence is a natural or unnatural analogue. Also, one or more amino acids in the sequence may be chemically modified, e.g. to increase physical stability or to lower susceptibility to enzymic, particularly protease or kinase, activity.

Also provided are antibodies that are specifically reactive against the polypeptides of the invention. Methods for producing antibodies are well known in the art. An antibody specific for the polypeptide of the invention can be easily obtained by immunizing an animal with an immunogenic amount of the polypeptide. Therefore, an antibody recognizing the polypeptide of the invention embraces polyclonal antibodies and antiserum which are obtained by immunizing an animal, and which can be confirmed to specifically recognize the polypeptide of the invention by Western blotting, ELISA, immunostaining or other routine procedure known in the art.

It is well known that if a polyclonal antibody can be obtained by sensitization, a monoclonal antibody secreted by a hybridoma may be obtained from the lymphocytes of the sensitized animal (Chapter 6, Antibodies A Laboratory Manual, Cold Spring Harbor Laboratory Press, 1988). Therefore, monoclonal antibodies recognizing the polypeptide of the invention are also provided. Methods of producing polyclonal and monoclonal antibodies are known to those of skill in the art and described in the scientific and patent literature, see, e.g., Coligan, Current Protocols in Immunology, Wiley/Green, N.Y. (1991); Stites (eds,) Basic and Clinical Immunology (7th ed.) Lange medical Publications, Los Altos, Calif., and references cited therein (Stites); Goding, Monoclonal Antibodies: Principles and Practice (2nd ed.) Academic Press, New York, N.Y., (1986); and Kohler (1975) Nature 256: 495. Such techniques include selection of antibodies from libraries of recombinant antibodies displayed in phage or similar on cells. See, Huse (1989) Science 246: 1275 and Ward (1989) Nature 341: 544. Recombinant antibodies can be expressed by transient or stable expression vectors in mammalian cells, as in Norderhaug (1997) J. Immunol. Methods 204: 77-87.

In this invention, an antibody also embraces an active fragment thereof. An active fragment means a fragment of an antibody having activity of antigen-antibody reaction. Specifically named, these are active fragments, such as F(ab')2, Fab', Fab, and Fv. For example, F(ab')2 results if the antibody of this invention is digested with pepsin, and Fab results if digested with papain. Fab' results if F(ab')2 is reduced with a reagent such as 2-mercaptoethanol and alkylated with monoiodoacetic acid. Fv is a mono active fragment where the variable region of heavy chain and the variable region of light chain are connected with a linker. A chimeric antibody is obtained by conserving these active fragments and substituting the fragments of another animal for the fragments other than these active fragments. In particular, humanized antibodies are envisioned.

The nucleic acid and polypeptide sequences investigated herein have been found to be differentially expressed in samples obtained from metastatic cancer cell lines and are predictive of tenascin-W expression in metastatic cancer tissue, as well as in other types of cancer and diseases.

Accordingly, certain aspects of the present invention relate to nucleic acids differentially expressed in tumour tissue, especially metastatic cancer cell lines, polypeptides encoded by such nucleic acids, and antibodies immunoreactive with these polypeptides, and preparations of such compositions.

Moreover, the present invention provides diagnostic and therapeutic assays and reagents for detecting and treating disorders involving, for example, aberrant expression of the subject nucleic acids.

Thus, in a further aspect of the invention, a composition is provided comprising an isolated nucleic acid molecule encoding tenascin W or a fragment thereof and a pharmaceutically acceptable excipient, diluent or carrier. The pharmaceutical use of nucleic acids encoding tenascin W has not previously been suggested and therefore in this embodiment, the nucleic acids of the pharmaceutical compositions are not limited to the nucleic acids of the invention. In particular, the composition may comprise and isolated nucleic acid having a nucleotide sequence selected from the group consisting of:
- (a) a nucleotide sequence as set forth in SEQ ID NO.1 or SEQ ID NO.3 (encoding human tenascin W);
- (b) a nucleotide sequence encoding the amino acid sequence shown in SEQ ID NO:2 or SEQ ID NO:4;
- (c) a nucleotide sequence with at least 35% identity, preferably at least 40, 50, 60, 70, 80, 90, 95 or 100% identity to any one of the sequences of (a) or (b), preferably (a);
- (d) a subsequence of at least 10, 15, 20, 25, 30, 40, 50, 75, 100 or more consecutive nucleotides of the sequence of (a), b) or (c); and
- (e) a nucleotide sequence complementary to (a), (b), (c), or (d), and a pharmaceutically acceptable excipient, diluent or carrier.

In one embodiment, the nucleic acid molecule encodes tenascin-W having the amino acid sequence as set forth in SEQ ID NO.2 or SEQ ID NO.4 or an amino acid with at least 30%, preferably at least 50%, 70%, 80%, 90%, 95%, or 100% identity to a sequence corresponding to SEQ ID NO:2 or 4. The nucleic acid molecules are at least 10, preferably at least 15, 20, 30, 50, 75, 100 or more consecutive nucleotides of SEQ ID NO:1 or SEQ ID No.2 or a sequence complementary thereto.

In one embodiment, the invention provides a composition comprising a nucleotide sequence fragment selected from the group consisting of nucleotides 2380-3171 of SEQ ID NO:1 or nucleotides 2371-3162 of SEQ ID NO:3, a complement of nucleotides 2380-3171 of SEQ ID NO:1 or of nucleotides 2371-3162 of SEQ ID NO:3, and RNA equivalents thereof, which encode an epitope for the binding with an antibody paratope.

In another embodiment, the nucleic acid molecule preferably encodes a protein having stem cell differentiation inducing activity. Although it is well within the skill of the art to identify polypeptides with the appropriate activity using routine methodology, the isolated nucleic acid molecule preferably encodes the amino acid sequence shown in SEQ ID NO:2 or SEQ ID NO:4, most preferably that of SEQ ID NO:4.

In yet another embodiment, the nucleic acid molecule has a subsequence that is antisense to SEQ ID NO:1 or SEQ ID NO:3, wherein the nucleic acid molecule may comprise nucleotide residues that are resistant to nuclease degradation.

The nucleic acid may be antisense to all or a part of a nucleic acid which hybridizes under stringent conditions to SEQ ID NO:1 or SEQ ID NO:3, or antisense to a sequence having at least 70% identity with SEQ ID NO:1 or SEQ ID NO:3, that is able to hybridize under low stringency conditions to SEQ ID NO:1 or SEQ ID NO:3, and which encodes tenascin-W. Low stringency conditions employs around 0.01×SSC buffer compared to high stringency which employs about a 10 fold greater concentration. Alternatively, the antisense RNA may be antisense to regulatory sequences of the tenascin-W gene, in particular to 5' upstream sequences (promoter region) of the gene. Similarly, small RNAI oligolucleoties can be designed to inhibit expression of Tenascin-W in a specific manner.

The nucleic acids can be RNA or DNA, sense or antisense, and in some embodiments, double stranded (including siRNA) or single stranded. In certain embodiments at least some of the nucleotide residues of the nucleic acids (sense or antisense) may be made resistant to nuclease degradation and these can be selected from residues such as phophorothioates and/or methylphosphonates.

The antisense nucleic acids as hereinbefore described can advantageously be used as pharmaceuticals, preferred pharmaceutical applications being for the manufacture of a medicament for the prophylaxis or treatment of conditions dependent on elevated Tenascin W levels, such as cancer.

Thus, the invention also provides a method of preventing or treating a condition dependent on Tenascin W, comprising administering to an individual in effective amount of a nucleic acid, as hereinbefore described. Thus, the invention encompasses the use of such nucleic acid molecules as a pharmaceutical as well as for the manufacture of a medicament, in particular for the prophylaxis or treatment of cancer or bone pathologies.

In yet another aspect, the present invention provides expression vectors capable of replicating in a host cell, comprising one or more vector sequences and a nucleic acid sequence encoding teneurin-W. The construct for use as a pharmaceutical is also provided, as well as its use for the manufacture of a medicament for the prophylaxis or treatment of cancer or the prophylaxis or treatment of bone pathologies.

Other embodiments of the invention include nucleic acid constructs capable of replicating in a host cell, comprising (a) at least one nucleic acid sequence portion encoding a tenascin-W protein or polypeptide of the invention (b) antisense nucleic acids as hereinbefore described or their complement, for example, if expression of the anitisense RNA in a cell is foreseen), or (c) nucleic acids as hereinbefore described and at least one nucleic acid sequence encoding a protein other than tenascin-W (or its homologues), e.g. vector sequence. Such constructs are not naturally occurring sequences. The constructs lack essential sequences of DNA which might permit them to function as vectors but are not naturally occurring as "hybrid" nucleic acids. They may include nucleic acid sequences that function as linkers or restriction sites which include without limitation a transcriptional regulatory sequence operably linked to a nucleotide sequence of the invention so as to render said nucleic acid construct capable of replicating in a host cell. Preferred constructs are synthesised using methods of oligonucleotides synthesis well known to those of skill in the art.

Also provided are vectors comprising a construct as hereinbefore described. Preferred vectors are expression vectors, preferably plasmids or viruses although cloning vectors are also provided for, optionally in the form of plasmids.

The invention provides host cells containing vectors. Preferred host cells are eukaryotic cells, more preferably insect cells or mammalian cells.

Constructs, vectors and transformed host cells of the invention are of use as pharmaceuticals, as well as for the manufacture of a medicament for the prophylaxis or treatment of a condition dependent on tenascin W, such as cancer or bone disorders.

Similarly, in a further aspect of the invention, a composition is provided comprising tenascin W, preferably recombinant tenascin-W, or a fragment thereof and a pharmaceutically acceptable excipient, diluent or carrier. In preferred embodiments, the tenascin-W is a polypeptide having an amino acid sequence selected from the group consisting of:
(a) an amino acid sequence as set forth in SEQ ID NO:2 or 4;
(b) an amino acid sequence with at least 35% identity, preferably at least 50%, 70%, 80%, 90%, 95%, or 99% identity, to the sequence of (a); and
(c) a subsequence of at least 5, 10, 15, 20, 30, 50, 75, 100 or more consecutive amino acids of the sequence of (a) or (b).

Preferably, the polypeptide has stem cell differentiation inducing activity as described above. More preferably, the polypeptide is encoded by the amino acid sequence shown in SEQ ID NO:4.

Thus, also provided is the use of tenascin-W for the treatment or prophylactic treatment of any disease or condition requiring increased tenascin-W levels, e.g. thrombosis, wound healing or atherosclerosis, as well as a condition ameliorated by the promotion of osteogenesis, e.g. bone healing, osteoporosis, as well as the use of tenascin-W as a stem cell marker. In yet a further aspect, the tenascin-W protein is used as a pharmaceutical.

The present invention further provides the use of a tenascin-W, e.g. for the manufacture of a medicament, for the prevention or prophylactic treatment of tumorigenesis or the treatment or prophylactic treatment of turnouts or cancer. The invention also includes the use of the tenascin-W for the manufacture of a medicament for the treatment or prophylactic treatment of any one or more of bone disease, rheumatism, asthma, allergic diseases, autoimmune diseases, prevention of transplant rejection and any other diseases involving tenascin e.g. thrombosis, cancer, wound healing and arthrosclerosis.

The invention therefore provides pharmaceutical compositions for humans or veterinary compositions for animal use that comprise one or more of the aforementioned active fragments of tenascin-W. The compositions may also include other active or non-active agents. Non-active agents may include a pharmaceutically acceptable excipient, diluent or carrier, but not limited to saline, buffered saline, dextrose and water.

The compositions and medicaments of the invention may therefore be used prophylactically in order to prevent tumours from forming, or they may be used in a curative or partly curative way to treat or contain a pre-existing tumourous condition. As well as tumours, cancerous or malignant conditions may be prevented or treated with compositions or medicaments of the invention.

In a particular aspect, the present invention provides the use of the nucleic acid or proteins or polypeptides as hereinabove described, for radioimmunotherapy. Use of radiolabeled antibody is a promising approach to target radiotherapy directly into the tumor. Anti-tenascin-C antibodies are currently tested in phase 1 and 11 clinical trials. Patients with malignant gliomas were administrated locoregional radioimmunotherapy (LR-RIT) using $^{131}$I labeled anti-tenascin antibody injected directly in the tumor (Riva et al., 1999a). The first results show that LR-RIT can be safely performed, with good results especially in patients with minimal disease. Similar approach was performed with $^{90}$Y (a pure beta emitter)-labeled antibodies Riva et al., 1999b), with promising results. Potentially more efficient radioimmunotherapies were shown to be possible using other isotopes, like in the case of an $^{211}$At-labeled anti-tenascin antibody (Zalutsky et al., 2001), without excessive toxicity for the patient. It is as well a useful tool for precise imaging of tumors, since the presence of isotopes specifically targeted into the tumor allows sequential scintigraphies of the tumor (Riva et al., 1999a), and makes possible a direct estimation of the success of the therapy. Similar methodologies can be applied using antibodies specific for tenascin-W.

The tumours or tumour cells of the present invention are preferably those which express tenascin-W in the stroma. In particularly preferred embodiments the tumours are solid tumours, e.g. mesenchymal tumours such as osteosarcoma, glioblastoina or epithelial cancers such as breast, prostate, lung and colorectal carcinoma.

The invention further provides the use of tenascin-W for the treatment or prophylactic treatment of a condition ameliorated by the promotion of osteogenesis, e.g osteoporosis, osteoarthritis, treatment of cartilage and bone pathologies. A protein or polypeptide as hereinabove described may be used to be incorporated into implants including without limitation hip joints, knee joints, or broken bones, to promote osteogenesis.

The invention also provides a method of preventing or prophylactic treatment of tumourigenesis or of treatment or prophylactic treatment of tumours or cancer or of any one or more of rheumatism, asthma, allergic diseases, autoimmune diseases, prevention of transplant rejection or the treatment or prophylactic treatment of any disease involving tenascin-W, e.g., thrombosis, wound healing and atherosclerosis in an individual comprising administering an effective amount of a tenascin-W or a fragment thereof.

The invention also provides a method of treatment or prophylactic treatment of a condition ameliorated by the promotion of osteogenesis, e.g osteoporosis, osteoarthritis, treatment of cartilage and bone pathologies in an individual comprising administering an effective amount of tenascin-W or a fragment thereof.

The determination of an effective dose is well within the capability of those skilled in the art. For any compound, the therapeutically effective dose can be estimated initially either in cell culture assays or in an appropriate animal model. The animal model is also used to achieve a desirable concentration range and route of administration. Such information can then be used to determine useful doses and routes for administration in humans.

A therapeutically effective dose refers to that amount of active agent which ameliorates the symptoms or condition. Therapeutic efficacy and toxicity of such compounds can be determined by standard pharmaceutical procedures in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by the individual physician in view of the patient to be treated. Dosage and administration can be adjusted to provide sufficient levels of the active moiety or to maintain the desired effect. Additional factors which may be taken into account include the severity of the disease state (e.g. tumour size and location); age, weight and gender of the patient; diet; time and frequency of administration; drug combination(s); reaction sensitivities; and tolerance/response to therapy. Long acting pharmaceutical compositions can be administered on a daily basis, every 3 to 4 days, every week, or once every two weeks, depending on half-life and clearance rate of the particular formulation.

The present inventors have observed stem cells, especially the periosteum, the stem cell compartment for osteogenesis, expressing tenascin-W and therefore also encompassed by the invention is a method of the invention, wherein tenascin-W is used as a stem cell marker for cells including without limitation osteogenic precursor cells in the bone marrow. Therefore, also provided is a method of selecting stem cells or progenitor cells having the ability to differentiate into osteoblasts from other cells, not having this ability. Stem cells expressing tenascin-W can be detected by an antibody. The antibody recognizing tenascin-W can be detected using secondary antibodies specific for the tenascin-W antibody, which are optionally labelled with a radiolabel, an enzyme, avidin or biotin, or fluorescent materials (e.g. green fluorescent protein (GFP) or rhodamine), for example. The cells are characterized by having tenascin-W expression above basal levels and are preferably selected from a mixed population of cells using the fluorescence-activated cell sorter (FACS) (see for example Abe et al., Dev. Biol. 1996; 180(2):468-72). The selected cells therefore carry a protein detectable by fluorescence. The sorted cells are useful for the production of biological parts of the body, e.g. bone tissue.

Also provided are antibodies that specifically recognizes tenascin W for use as a pharmaceutical, as well as for the manufacture of a medicament, for the prophylaxis or treatment of cancer (e.g., glioblastoma, prostate, lung, colorectal, osteo-or breast carcinoma), including metastatic cancer, or for the prophylaxis or treatment of any disease or condition involving tenascin-W, e.g. excessive bone growth. In another aspect of the present invention, an antibody specifically reactive against tenascin-W or a fragment thereof, and the use of an antibody for the manufacture of a medicament for the prophylaxis or treatment of cancer, and the antibody for use as pharmaceutical is provided.

Antibodies that specifically recognize tenascin-W or a fragment thereof are also provided, in particular antibodies that recognise the above mentioned epitope.

Methods for detecting tenascin-W embrace, for example, the use of an antibody as referred to above, optionally with the use of an enzyme reaction. The antibody recognizing tenascin-W can be detected using secondary antibodies specific for the tenascin-W antibody, which are optionally labelled with a radiolabel, an enzyme, avidin or biotin, or fluorescent materials (FITC or rhodamine), for example.

Also encompassed by the invention is the use of an antibody that specifically recognizes tenascin-W for the manufacture of a medicament, in particular a medicament for the prophylaxis or treatment of cancer, the prophylaxis or treatment of bone disease, or as a pharmaceutical. In particularly encompassed by the invention is the use of an antibody that specifically recognizes tenascin-W for the diagnosis of tumour, especially metastatic tumour.

In a further embodiment, the present invention provides a method for identifying agents for the prevention or the prophylactic treatment of tumourigenesis or the treatment or prophylactic treatment of tumours or cancer, or the treatment or prophylactic treatment of any disease or condition involving tenascin-W, e.g. a condition ameliorated by the promotion (or inhibition) of osteogenesis, comprising contacting a test compound with a tenascin-W expressing sample and then measuring a change in one or more of (a) cell proliferation, e.g. cell progression entering S-phase of the cell cycle; (b) DNA synthesis; (c) cell adhesion; (d cell spreading; (e) focal adhesion and actin stress fibre formation on fibronectin; (f) cell binding to extracellular matrix (ECM), relative to when said test compound is absent.

Cells may be encouraged to proliferate by the addition of tenascin-W to the cell culture, preferably by coating the solid substrate therewith. A substrate can be any surface that promotes cell adhesion. The solid substrate may also be coated by other EMC which include without limitation fibronectin, collagen, etc. The cell cultures are preferably grown on a solid substrate or in a liquid medium. A first measurement of one or more of (a) to (f) may be made prior to contacting the cells with a test substance. A second measurement may be made thereafter, A multiplicity of further measurements may be made over a period of hours or days after contact of the cells with the test compound. In this way a time course of the cellular response(s) may be obtained and analysed.

In one preferred embodiment of the present invention, the presence of tenascin-W in the liquid medium is measured relative to when a test compound is absent. An increase in the level of tenascin-W present in the medium relative to when said test agent is absent correlates to an agent effective in the promotion of osteogenesis, for example. A decrease in the level of tenascin-W present in the medium relative to when said test agent is absent correlates to an anti-proliferative or anti-tumour agent, or an agent effective in inhibiting osteogenesis or osteoblast formation.

In preferred aspects one or more of the following conditions arising after contacting cells with a test compound is indicative of an anti-proliferative or anti-tumour agent, or an inhibitor of osteoblast formation:
  (a) a reduction in cell proliferation; or a decrease in the proportion of cells entering S-phase of the cell cycle;
  (b) a reduction in CNA synthesis;
  (c) an increase in cell adhesion,
  (d) an increase in cell spreading;
  (e) an increase in focal adhesion and actin stress fibre formation on fibronectin; and
  (f) an increase in the binding of cells to ECM, preferably fibronectin;

In other preferred aspects one or more of the following conditions arising after contacting cells with a test compound may indicate an osteogenesis promoting agent:
  (a) an increase in cell proliferation; or an increase in the proportion of cells entering S-phase of the cell cycle;
  (b) an increase in DNA synthesis;
  (c) and (d) an increase in the expression of bone-specific markers such as alkaline phosphatase activity, calcification or any others known in the art (e.g., Raouf and Seth, 2002 Bone 30: 463-71).

Actin stress fibre formation may be assayed according to the Actin Assembly Assay described in Bloom, L. et al 1999) Mol Biol Cell 10: 1521-1536. Adhesion assays may be performed according to the method described in Bloom, L. et al (1999).

In other embodiments, the method of the invention may further comprise control cells grown in the absence of test substance and (a), (b), (c), (d), (e), and/or (f) are measured in both control and test cultures. The test measurements can thereby be normalised with respect to the control.

The screening method further provides an essentially cell-free system for the identification of potential anti-tumour or tumour preventing agents or for an agent inhibiting osteogenesis. This method relies on the ability of a potential anti-tumour agent to prevent, inhibit or disrupt the binding between an ECM and tenascin-W. The nature of any disruption of the ECM and tenascin-W binding may be determined by performing a binding assay for ECM and tenascin (see e.g.

example 10). For example, calorimetric methods may be used or measurement of labelled reagents.

Alternatively, a method is provided for identifying modulators of tenascin W function, comprising: (a) contacting a test compound with tenascin W and/or alpha8 beta1 integrin, and (b) measuring the binding of the test compound to tenascin-W and/or alpha8 beta1 integrin, or (c) measuring a disruption of binding of tenascin-W to alpha8 beta1 integrin, relative to when the test compound is absent. A decrease in binding of tenascin-W to alpha8 beta1 integrin is indicative of an inhibitor of this interaction, and increased binding could indicated that the test compound activates the alpha8 beta1 integrin, thereby increasing the interaction between tenascin-W and alpha8 beta1.

The relative amounts or concentrations of reagents and test substance may be varied, thereby permitting calculation of inhibition constants and other parameters, e.g. binding affinities. The optimisation of assay conditions will be well within the realm of one of ordinary skill in the art. The system may further comprise a control without test substance and the binding is measured in the control, thereby permitting corresponding measurements in the test system to be normalised relative to the control.

Where one component of the assay (screening) systems of the invention is coupled to a solid particle or substrate, then one or more of the other components not so coupled may be labelled. Examples of labels include radiolabels e.g. $^{14}C$ or $^{3}H$, dyes, metal sols, enzymes or biotin/avidin. By attaching such labels to "free" components in the system any binding assay may be carried out in solution in accordance with procedures well known in the art. After allowing the components to react solid phase particles can be separated from solution, e.g. by filtration or sedimentation (including centrifugation). In some embodiments immunoprecipitation may be used to separate bound and free labelled components. Usually, an antibody may be employed to bring an unlabelled component out of solution (whether or not this component has bound to another labelled component or not). After separation, the label present in solution (free) and the label present in or on the solid phase (bound) may be measured. Standard analyses of such bound and free data, e.g. Scatchard plots and the determination of affinity and inhibition constants for binding are well known to the person of ordinary skill in the art.

Where the solid phase is not particulate, e.g. in the form of a surface, such as a microtiter plate well, then binding assays measuring bound and free label may be performed but this will normally involve the removal of liquid phase from the wells after binding reactions have occurred. Advantageously, this assay format may dispense with the need for providing specifically labelled reaction components. Instead, labelled antibodies may be used to measure the binding of previously free reaction components to solid phase components.

In some embodiments the tenascin-W molecule, variant or fragment thereof may be attached directly to a solid phase. In preferred immunoassay embodiments of this type, tenascin-W bound to an ECM is measured using an antibody reactive against tenascin-W.

Immunological binding assays are known in the art. For a review, see Methods in Cell Biology Vol. 37: Antibodies in Cell Biology, Asai, (Ed.) Academic Press, Inc. New York (1993).

A label may be any detectable composition whereby the detection can be spectroscopic, photochemical, biochemical, immunochemical, physical or chemical. For example, useful labels can include $^{32}P$, $^{35}S$, $^{3}H$, $^{14}C$, $^{125}I$, $^{131}I$, fluorescent dyes (e.g. FITC rhodamine and lanthanide phosphors), electron-dense reagents, enzymes, e.g. as commonly used in ELISA (e.g. horseradish peroxidase, beta-galactosidase, luciferase and alkaline phosphatase), biotin, dioxigenin, or haptens and proteins for which antisera or monoclonal antibodies are available. The label may be directly incorporated into a target compound to be detected, or it may be attached to a probe or antibody which binds to the target.

Throughout the assays of the invention, incubation and/or washing steps may be required after each application of reagent or incubation of combinations of reagents. Incubation steps may vary from about 5 minutes to several hours, perhaps from about 30 minutes to about 6 hours. However, the incubation time usually depends upon the assay format, analyte, volume of solution, concentrations, and so forth. Usually, the assays should be carried out at ambient temperature, although they may be conducted at temperatures; in the range 10° C. to 40° C., for example.

A particularly preferred assay format is an enzyme-linked immunosorbent assay (ELISA).

All of the aforementioned methods of screening of the invention are equally applicable to the screening of substances for biological activity and potential agents for any other disease or condition involving tenascin-W, e.g. wound healing or treatment of atherosclerosis.

Also included within the scope of the present invention are anti-tumourigenic, anti-tumour, anti-metastastic, (anti-)osteogenic, wound healing or anti-artherosclerosis substances or substances for the treatment or prophylactic treatment of any disease or condition involving tenascin-W identified by any of the screening methods of the invention. These substances may be proteins, polypeptides or small organic molecules (drugs). The invention therefore includes pharmaceutical compositions for preventing or treating tumours, metastasis, or bone pathologies and comprising one or more of the substances identified by a method of the invention. For example, inhibitors of tenascin-W expression or activity are considered potential ant-cancer agents, whereas tenascin W or agonists thereof are considered agents effective in promoting osteogenesis, which can be used in vivo or ex vivo.

Thus, the present invention provides a novel mammalian member of the tenascin family and uses thereof. It permits the identification of agents effective against conditions dependent on tenascin-W, in particular anticancer agents or agents that promote osteogenesis, by performance of any of the methods of screening described herein. Preferred anti-cancer agents are those which inhibit proliferation of the cancer cells and which may be general anti-proliferative agents.

The invention includes all nucleic acid molecules and proteins and polypeptides as hereinabove described, as well as agents identified by performing the methods, and the use of these agents as pharmaceuticals, particularly as medicaments for the prophylaxis or treatment of cancer and other conditions dependent on tenascin W.

Thus, in a further aspect the invention provides for the use of tenascin-W and of an agent identified by a screening method of the invention as a pharmaceutical.

The invention further provides tenascin-W for an agent identified by a screening method of the invention, for the manufacture of a medicament for the prophylaxis or treatment of a condition dependent on tenascin-W, for use to treat cancer or bone diseases or an immunological defect.

The invention provides a method of preventing or treating a condition dependent on tenascin-W comprising administering to an individual an effective amount of a construct, vector, host cell or antibody described above.

The invention also provides a method of inhibiting a condition dependent on tenascin-W comprising administering an effective amount of the modulator identified by a screening method of the invention described above, for the treatment of cancer or bone disease or an immunological defect.

Also provided by the invention are the nucleic acid molecules, the proteins, and the agents referred to above in a pharmaceutical composition, possibly in the presence of suitable excipients known to one of ordinary skill in the art. The compositions may be administered in the form of any suitable composition as detailed below by any suitable method of administration within the knowledge of a skilled man. The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and nontherapeutic. Examples of such excipients are saline, Ringers solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

Any protein is administered at a concentration that is therapeutically effective to prevent allograft rejection, GVHD, allergy and autoimmune diseases. The dosage and mode of administration will depend on the individual. Generally, the compositions are administered so that the functional protein is given at a dose between 1 pg/kg and 10 mg/kg, more preferably between 10 ug/kg and 5 mg/kg, most preferably between 0.1 and 2 mg/kg. Preferably, it is given as a bolus dose. Continuous short time infusion (during 30 minutes) may also be used. The compositions according to the invention may be infused at a dose between 5 and 20 μg/kg/minute, more preferably between 7 and 15 ug/kg/minute.

According to a specific case, the "therapeutically effective amount" of a composition needed should be determined as being the amount sufficient to cure the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

The present invention also provides a method of diagnosing or prognosing cancer, or any other condition dependent on elevated tenascin-W levels, comprising, (a) analysing a sample obtained from an individual for the presence of tenascin-W; and (b) correlating the presence of tenascin-W with an unfavourable prognosis or diagnosis.

The methods of the present invention will typically involve the determination of the presence, level, or activity of tenascin-W in a cell or tissue sample, which sample will often be obtained from a human, but one can also readily understand that samples tested by the present method can be obtained from agriculturally important mammals, such as cattle, horses, sheep, etc., or other animals of veterinary interest, such as cats and dogs. The assay may be carried out on any cell or tissue sample, such as somatic tissues, germline tissues, or cancerous tissues, as well as on samples from body fluids, such as pleural fluid, blood, serum, plasma and urine. The method may also further comprise propagating cells in the sample in cell culture.

A "sample" is the material being analyzed which is usually, but not necessarily, subjected to pretreatment to provide the tenascin-W in assayable form. This would for example, entail forming a cell extract, methods for which are known in the art for example, see Scopes, Protein Purification: Principles and Practice, Second Edition (Springer-Verlag, N.Y., 1987)).

In the broader aspects of the invention, there is no limitation on the collection and handling of samples as long as consistency is maintained. The sample is obtained by methods known in the art, such as, biopsies, surgical resections, smears, or the like. Optionally, cells obtained in a sample may be propagated in cell culture.

Consistency of measurement of tenascin-W or tenascin-W activity in clinical samples can be ensured by using a variety of techiques. For example, to control for the quality of each tissue extract, another enzymatic activity, such as alkaline phosphatase, can serve as an internal control. In addition, an internal standard can be measured concurrently with tenascin-W in the sample as a control for assay conditions. Thus, the analyzing step can comprise detecting a control protein in the sample, optionally normalizing the value obtained for tenascin-W with a signal obtained with the control protein.

The presence of tenascin-W in the sample can be determined by detecting the tenascin-W protein using methods known in the art. In this invention, there are no limitations on the type of assay used to measure tenascin-W or tenascin-W activity. For example, tenascin-W can be detected by immunoassays using antibodies specific for tenascin-W. The antibody can be used, for example in Western blots of two dimensional gels where the protein is identified by enzyme linked immunoassay or in dot blot (Antibody Sandwich) assays of total cellular protein, or partially purified protein.

Methods for sample concentration and protein purification are described in the literature (see Scopes, 1987). For example, if desired, the tenascin-W present in the cell extract can be concentrated, by precipitating with ammonium sulfate or by passing the extract through a commercially available protein concentration filter, e.g., an Amicon or Millipore, ultra-filtration unit. The extract can be applied to a suitable purification matrix, such as an anion or a cation exchange resin, or a gel filtration matrix, or subjected to preparative gel electrophoresis. In such cases, the tenascin-W and protein yield after each purification step needs to be considered in determining the amount of tenascin-W in a sample.

Tenascin-W may be detected using an antibody specific for tenascin-W, and a control assay can be carried out using an antibody specific for another tenascin molecule. Optionally, the method may further comprise correlating in an increase in tenascin-W in the sample relative to healthy tissue. For example, tenascin-W can be detected using an antibody specific for tenascin-W expressed in tumour tissue and compared to antibody binding to any tenascin-W expressed (or non-specific reaction) in healthy tissue.

The sample is preferably a tissue sample mounted onto a solid surface for histochemical analysis. The presence of detectable, accessible tenascin-W indicates that tenascin-W is accessible to cells for binding. This leads to a unfavourable diagnosis or prognosis. If, on the other hand, the antibody does not react with tenascin-W in the tissue section, then there is an expectation that tenascin-W is not present. This leads to a favourable diagnosis or prognosis.

The present inventors have found that tenascin-W is specifically expressed in solid tumours, in particular metastatic tumour tissue or stroma thereof. The presence of tenascin-W therefore indicates a cancerous condition, in particular the presence of metastatic tumour tissue, whereas the absence of tenascin-W indicates healthy tissue or non-metastatic tumour tissue. Tenascin-W was identified in developing mouse tissues by western blotting. High expression of tenascin-W was found in the metastatic tumours of ras-transgenic mice, but not in the myc-or neuT-transformed non-metastatic tumours. The presence of tenascin-W (170 kD) is indicative of unfavourable diagnosis.

In a further embodiment, the diagnostic and prognostic methods of the invention further comprises analysing the sample for the presence of alpha 8 integrin, the presence of alpha 8 integrin correlating with an unfavourable prognosis or diagnosis. This can easily be achieved, for example, using an antibody as described in detail in Example 8 below.

In a preferred embodiment, the invention provides kits suitable for use in the diagnostic or prognostic methods of the invention. Such kits comprise reagents useful for carrying out these methods, for example, antibodies from one or more species specific for tenascin-W and alpha 8 beta1 integrin. Secondary antibodies that recognise either or both such primary anti-fibronectin antibodies can also be included for the purpose of recognition and detection of primary antibody binding to a sample. Such secondary antibodies can be labelled for detection e.g. with fluorophores, enzymes, radioactive labels or otherwise. Other detection labels will occur to those skilled in the art. Alternatively, the primary anti-tenascin-W antibodies can be labelled for direct detection.

The invention is further described below, for the purpose of illustration only, in the following examples.

EXAMPLE 1

Cloning of Mouse Tenascin-W

Mouse tenascin-W was cloned from a cDNA library of 19d whole mouse embryos (DupLEX-A DLM-110; OriGene Inc.) In a first step the following PCR primers derived from a sequence from chromosome 1, similar to Tenascin-R (Accession number AL049689) were used for nested PCR reactions with the Expand High Fidelity PCR System (Roche) using the mouse cDNA library as template. The first reaction was performed with the primer set 5'-TAGCAGCCCACAGCATC-TACTTGCC-3' (SEQ ID NO:5)/5'-ATTGCTGTTCTGCT-GAACCTGACTGCA-3' (SEQ ID NO:6) and the second reaction with 5'-ATGGATCCAGAAATTGACGGC-CCCAAAAACCTAG-3' (SEQ ID NO:7)/5'-ATAAGCT-TGTGGAGAGGGTGGTGGATACATTTC-3'(SEQ ID NO:8). The second primer set included a BamHI and a HindIII restriction site, respectively, to allow the directed cloning into the bacterial expression vector pQE30 (Qiagen) supplying a C-terminal His-tag for the purification of the recombinant proteins.

The mouse proteins (tenascin W polypeptide fragments obtained as a result of the above procedure) were expressed in *E. coli* and purified by affinity chromatography to a Ni-NTA matrix (Qiagen) according to the matrix supplier's manual. The protein was purified under native conditions and was elated with 250 mM imidazole.

Full length tenascin-W was cloned by the use of mouse tenascin-W specific primers derived from the above mouse tenascin-W cDNA and primers matching the vector of the same 19d whole mouse embryo cDNA library used before. To obtain the complete 5' sequences, the following PCR reactions using the above cDNA as template were performed: The first PCR reaction was performed using the primer pair 5'-AGGAGATGGTGGCTGTATTTTCGG-3' (SEQ ID NO:9)/5'-AGCCTCTTGCTGAGTGGAGATGCC-3' (SEQ ID NO:10) followed by a second PCR reaction with the primer set 5'TAGAATTCGGTCACCTGATTGGTCAC-TAGG-3' (SEQ ID NO:1)/5'-TTATGATGTGCCAGATTAT-GCC-3' (SEQ ID NO:12). To complete the 3' part of the tenascin-W cDNA the following PCR reactions were performed: In the first reaction the primer pair 5'-CTCAAAAT-TGATGGCTACATTTTGACC-3' (SEQ ID NO:13)/5'-MGCCGACAACCTTGATTGGAGAC-3' (SEQ ID NO:14) was used followed by the primer pair 5'-TACCAGTTC-CCAAATGGCACCG-3' (SEQ ID NO:15)/5'-AAAC-CTCTGGCGMGAAGTCC-3' (SEQ ID NO:16). In each case the longest products were cloned. These overlapping tenascin-W cDNA clones were assembled into one full length mouse tenascin-W cDNA and cloned into the expression vector pCEP/Pu (see Kohfeldt et al. (1997).

FEBS Left. 414:557-61). At the 3' end of the tenascin-W cDNA a 6xHis-tag was inserted in front of the stop codon to allow the purification of full length mouse tenascin-W protein expressed in mammalian cell culture.

The recombinant mouse tenascin-W protein comprises three C-terminal fibronectin type III repeats in the region defined by amino acids 794-1057 of the complete amino acid sequence of mouse tenascin-W, encoded by nucleotides 2380-3171 of the tenascin-W nucleotide sequence.

EXAMPLE 2

Characterization of Mouse Tenascin-W

The full length cDNA of mouse tenascin-W was cloned as described in example 1. The cDNA sequence encodes a typical member of the tenascin protein fairly and harbors from the N-terminus to the C-terminus of the protein the following structural domains: signal petide for secretion, N-terminal domain for dimerisation of two tenascin-W trimers that are assembled by heptad repeats. This results in a disulfide-linked hexameric protein complex where each subunit contains three and a half EGF-like repeats, nine fibronectin type III repeats, and a fibrinogen-like C-terminal globular domain.

The full length tenascin-W cDNA was transfected into HEK 293 cells using the transfection reagent fugene (Roche). Transfected cells were selected with puromycin and the medium containing the secreted tenascin-W protein was collected and the protein was purified by sequential chromatography over a gelatin-agarose column (Sigma) to remove any contaminating fibronectin in the preparation and by adsorption to a Ni-NTA matrix (Qiagen). The tenascin-W was eluted from the nickel column by 250 mM imidazole.

The recombinant protein was also analyzed by SDS-PAGE (sodium dodecyl sulfate-polyacrylamide gel electrophoresis) on 6% polyacrylamide gels, under reducing and non-reducing conditions as well as by electron microscopy after rotary shadowing using the same procedure as described for tenascin-C (Chiquet-Ehrismann, R. et al. (1988) Cell 53, 383-3901). Tenascin-W showed a similarly slow migration as the hexameric tenascin-C protein. Electronmicrographs of tenascin-W after rotary shadowing indeed revealed hexameric molecules with six subunits of about 50 nm length radiating from a central globular domain.

EXAMPLE 3

Cloning of Human Tenascin-W

Human tenascin-W was cloned from cDNA made from mRNA isolated from the osteosarcoma cell line Saos-2 (ATCC; HTB 85) essentially as described in Example 1 using the same PCR primers. The human protein was expressed and purified by affinity chromatography to a Ni-NTA matrix (Qiagen) according to the matrix suppliers manual. The protein was purified under native conditions and was eluted with 250 mM imidazole.

The recombinant protein comprises the three C-terminal fibronectin type III repeats in the region defined by amino acids 791-1054 of the complete amino acid sequence of human tenascin-W encoded by nucleotides 2371-3163 of the tenascin-W nucleotide sequence of the database entry AL049689), respectively.

Full length tenascin-W is cloned by the use of human tenascin-W specific primers derived from the above human tenascin-W cDNA and human genomic sequences 5 to the ATG start codon of the cDNA sequence entry AL049689 using cDNA made from mRNA isolated from osteosarcoma cell line Saos-2 (ATCC; HTB 85) as the template. The following primers are used for three sets of nested PCRs:

hTNW1: 5'CATCCTGGAGGGTCTGCTCC3' (SEQ ID NO:17)

hTNW2: 5'GGGCAATTGGTGTCAGCTTTC3' (SEQ ID NO:18)

hTNW3: 5'GACTCGAGCTTTCCAAGGAT-GAGTCTCC3' (SEQ ID NO:19)

hTNW4: 5'GAGGATCCCCTGGTTGC-CCCTTTCAG3' (SEQ ID NO:20)

hTNW5: 5'GCGCTACACTTCTGCTGATG3'(SEQ ID NO:21)

hTNW6: 5'CTGTGGAGAGGGTGGTGG3' (SEQ ID NO:22)

hTNW7: 5'GACTCGAGTGCACAAGGATGAGAG-CAG3'(SEQ ID NO:23)

hTNW8: 5'GAGGATCCACCCTTAAAGGCAA-CAAGGG3'(SEQ ID NO:24)

hTNW8: 5'GAGGATCCACCCTTAAAGGCAA-CAAGGG3'(SEQ ID NO:24)

hTNW9:P 5'CGCAGTCTGGTGGCATATTG3'(SEQ ID NO:25)

hTNW10: 5'CATGATTTGTTCTGCGGGC3'(SEQ ID NO:26)

hTNW11:5'GACTCGAGCGGCTACATTCTGACT-TACC3'(SEQ ID NO:27)

hTNW12:5'GAGGATCCTCAGTGATGGTGATGGT-GATG3'(SEQ ID NO:28)

The following PCR reactions are performed using for fragment A primer combinations hTNW1/hTNW2 followed by hTNW3/hTNW4, for fragment B hTNW5/hTNW6 followed by hTNW7/hTNW8 and for fragment C hTNW9/hTNW10 followed by hTNW11/hTNW12. These three fragments can be joined together to make up the full length human tenascin-W by digesting fragment A with XhoI and AccI, fragment B with AccI/NarI and fragment C with NarI/BamHI and cloning the ligated assembly into the XhoI/BamHI sites of the expression vector pCEP/Pu (see Kohfedt et al. (1997) FEBS Lett. 414:557-61), At the 3'end of the human tenascin-W cDNA a 6×His-tag, was inserted in front of the stop codon for ease of purification upon expression in mammalian cell culture. Human tenascin-W is purified as described for mouse tenascin-W (example 2).

EXAMPLE 4

Antibody Production, Immunohistochemistry and Immunoblots: Expression of Tenascin-W during Development The bacterially expressed recombinant fragment of mouse tenascin-W as described above in Example 1, was used to raise polyclonal antisera in rabbits using standard immunization procedures. These antisera were used to detect tenascin-W in tissue extracts and cryosections of developing mouse embryos using methods described for tenascin-Y (Hagios, C. et al. (1996) J. Cell Biol. 134, 1499-1512). The antiserum reacted specifically with purified full-length recombinant tenascin-W as well as with endogenous tenascin-W in tissue extracts of mouse organs, as demonstrated by Western blotting. In both cases, tenascin-W was identified as a 170 kDa molecular weight species.

The anti-tenascin-W antiserum was used to investigate tenascin-W expression during normal mouse development by immunohistochemistry. For immunohistochemistry, tissues were fixed in ice-cold 4% paraformaldehyde in phosphate-buffered saline (PBS) overnight, washed with PBS and cryoprotected with 25% sucrose in PBS overnight at 4° C. The tissues were embedded in OCT (Optimal Cutting Temperature) mounting medium (Cat. No. 27050 OCT Compound by Ted Pella Inc., CA) and sections of 12-16 μm were cut and collected onto glass slides. The sections were air-dried for 2 hours before staining with anti-tenascin-W antiserum followed by a fluorescently labelled secondary antibody.

Tenascin-W first appears at embryonic day 11.5 (E11.5) in the maxillary process. Between: E14.5 and E16.5, tenascin-W and tenascin-C expression overlaps in developing connective tissue (palate and mandible) in the face and jaw. Furthermore tenascin-W is found in the extracellular matrix (ECM) of smooth muscle, mesothelia and bone. In the adult mouse tenascin-W is found in a subset of the tenascin-C-positive ECM of the aortic valve and the limbus. In these locations its expression coincides with the stem cell compartment of the respective tissue. Tenascin-W is also expressed in the periosteum, the stem cell compartment for osteogenesis. Tenascin-W is also expressed in kidney and the digestive tract in a subset of tenascin-C-positive regions, but not in the brain.

EXAMPLE 5

Monoclonal Antibodies against Human Tenascin-W

The bacterially expressed recombinant fragment of human tenascin-W as described above in Example 3 was used to raise monoclonal antibodies against human tenascin-W using standard procedures. The monoclonal antibodies reacted specifically with human tenascin-W having better binding than relying on the crossreactivity of the anti-mouse tenascin-W for human tenascin-W. The monoclonal antibodies are particularly useful to stain human tissues.

EXAMPLE 6

Tenascin-W Expression in Tumour Cells

Tenascin-W expression in tumour cells was tested and compared with the known results for tenascin-C which has been found to be highly expressed in tumour tissues (Chiquet-Ehrismann, R. (1993) Sem. Cancer Biol. 4, 301-310). Mouse mammary tumours develop readily in transgenic mice expressing oncogenes under the control of mammary gland-specific promoters. Overexpression of c-myc results in the growth of non-metastatic tumours whereas overexpression of Ha-ras leads to the development ot metastatic tumours (Li, F. et al. (1994) Int. J. Cancer 59, 560-568).

In this Example, the antisera described in Example 4 were used to detect tenascin-W in mouse mammary tumours as described fair tenascin-Y by Hagios, C. et al. (1996). High expression of tenascin-W (about 170 kDa) was found in the tumours of ras-transgenic mice (metastatic), but not in the myc-or neuT-transformed non-metastatic tumours, whereas tenascin-C was over-expressed in both types of tumours.

As a control, expression of tenascin-W was examined in healthy tissue, using blood serum, for example. The content of tenascin-W in serum is analyzed by Western blotting. For improved sensitivity a Sandwich ELISA test as described previously for tenascin-C (Schenk et al. 1995. Int. J. Cancer 61:443-449) can be used. Briefly, 96-well plates are coated with either polyclonal or monoclonal anti-tenascin-W antibodies. The serum samples are applied, the wells washed and the bound tenascin-W is detected by either a polyclonal or a monoclonal anti-tenascin-W antibody followed by an appropriate peroxidase-labeled secondary antibody. No expression of Tenascin-W was found in blood serum from wild-type mice. In contrast, healthy kidney, heart valve and periosteum was found to express Tenascin-W. Transgenic mice overexpressing neuT develop non-metastasizing mammary tumours, whereas in transgenic mice overexpressing neuT together with EphB4 receptor tyrosine kinase the turn ours are metastatic (Munarini, N. et al. (2002) Cell Sci. 115, 25-37). Using this model system we again found high expression of tenascin-W in metastatic tumours, but not in non-metastatic ones. These expression patterns were confirmed by SDS-PAGE (SDS-polyacrylamide gel electrophoresis), by fractionating tumour extracts, blotting on polyvinylidene difluoride membranes, and analyzing the extract using anti-tenascin-W antisera.

EXAMPLE 7

Adhesion Assay

The purified tenascin-W was used for cell adhesion studies of MDA-MB435 mammary carcinoma cells (ATTC; HTB-129), C2C12 mouse skeletal myoblasts (ATTC; CRL-1772, T98G glioblastoma cells (ATTC; CRL-1690) and NIH-3T3 fibroblasts (ATTC; (CRL-1658). In brief, 60-well microtiter plates (Nunc) were coated with 2-100 µg/ml tenascin-W for 1 h at 37° C. The non-coated plastic surface was blocked with 1% heat-inactivated BSA in PBS.

Cells were trypsinised, trypsin was blocked with 100 µl g/ml soybean trypsin inhibitor in PBS and, cells were resuspended in serum-free medium and counted. 200-500 cells per well were plated for the indicated time points, fixed by addition of glutaraldehyde (2% final concentration) for 15 minutes and stained with 0.1% crystalviolet in 20% methanol for 30 minutes. Cells were observed under a microscope (Nikon diaphot).

Most cells adhered to tenascin-W coated at 2-100 µg, whereas cell adhesion to tenascin-C was minimal.

We compared the morphology and actin cytoskeleton of C2C12 mouse skeletal myoblasts and T98G glioblastoma plated on tenascin-W to cells plated on fibronectin or tenascin-C. The shape of the cells on tenascin-W was very different from the cells on fibronectin, which became particularly evident after F-actin staining with phalloidin. The cells on libronectin were well spread containing stress fibers, whereas the cells on tenascin-W had many actin-rich processes but no stress fibers and the cell bodies remained relatively round.

EXAMPLE 8

Identification of a Cellular Tenascin-W Receptor

To determine the cellular receptor(s) responsible for cell adhesion to tenascin-W, we tested the effect of integrin function-blocking antibodies on adhesion of T98G glyoblastoma cells on tenascin-W. Antibodies to α1, α2, α3, α4, α5, α6 and αV were unable to inhibit adhesion of T98G cells to tenascin-W. Nevertheless, this adhesion was β1 integrin-dependent since 10 µg/ml of the anti-β1 integrin blocking antibody P4C10 (Sigma) was able to completely inhibit adhesion to tenascin-W.

IDG tripeptide motifs have been reported to be the recognition sequence for alpha9 betal integrin (Yokosaki et al., 1998). Since mouse tenascin-W contains three IDG motifs we investigated whether α9 integrin could be the receptor for tenascin-W. We plated SW480 colon carcinoma cells transfected either with an empty vector or with the vector containing the cDNA for α9 integrin (Yokosaki et al. J Biol. Chem. 1996 Sep. 27;271(39):24144-50) on tenascin-W coated wells. However, the α9-and mock-transfected SW480 cells failed to adhere to tenascin-W whereas they adhered well to fibronectin and collagen. integrin α8 is expressed in developing rib bone, in kidney and in smooth muscle from the gastrointestinal tract (Denda et al. Biochemistry. 1998 Apr. 21;37 (16):5464-74). Since this expression pattern coincides it the presence of tenascin-W it seemed that integrin α8 was a good candidate receptor for tenascin-W as well. We tested this hypothesis by using the leukemia cell line K562, transfected with a 8 integrin (Denda et al. Biochemistry. 1998 Apr. 21;37 (16):5464-74). Transfected K562 cells could indeed adhere to tenascin-W and the mock-transfected control cells did not. Therefore, α8⊕1 integrin is a receptor for tenascin-W.

EXAMPLE 9

DNA Replication and Proliferation Assay 96-well plates (Falcon) are coated as described above. Cells are serum starved overnight and trypsinised. $10^4$ cells are transferred onto the coated plates in the presence of 1% serum or 40 nM PDGF BB (Platelet-derived growth factor BB), 14 h later cells are labelled with radioactive $^3$H-thymidine (0.5 µCi/well) for 4 h at 37° C., incorporated $^3$H-thymidine precipitated with 10% TCA and determined with a Beckman scintillation counter after cell lysis in 0.3N NaOH, 2% SDS. Alternatively, incorporation of BrdU is measured or cells numbers are counted over a growth period of several days of cells plated on different substrates. Cancer cells grown on tenascin-W show an increased growth rate over cells plated on fibronectin, as established by counting cells or an increase in radioactive $^3$H-thymidine or BrdU incorporation into cellular RNA.

EXAMPLE 10

In Vitro Binding Assay (EUSA)

96-well ELISA plates are coated with the appropriate ECM proteins (e.g. fibronectin or tenascin-W) for 1 h at 37° C., blocked with 1% milkpowder, 0.05% Tween-20 in PBS. ECM proteins (tenascin-W or fibronectin) are added in blocking solution for 1 h, washed with blocking solution and the appropriate antibodies are added. In this way, an interaction between tenascin-W and fibronectin can be tested, for example. Bound proteins are detected by immune reaction with a peroxidase-coupled secondary antibody followed by colour reaction with 21 mg/ml citric acid 1-hydrate, 34 mg/ml $Na_2HPO_4.2H_2O$, 0.4 mg/ml phenylenediamine, 1 µl $H_2O_2$, which can be stopped with 4M sulphuric acid. The absorbance was read at 590 nm.

EXAMPLE 11

Immunofluorescence Microscopy $10^4$ cells are transferred onto 4-well Cellstar plastic plates (Greiner) that are coated with ECM proteins essentially as described above. Cells are fixed with 4% paraformaldehyde, 50 mM phosphate buffer, 5 mM ETDA in PBS for 15 minutes, blocked with 3% BSA, 0.5% Tween-20 in PBS and incubated with primary and secondary antibodies in blocking solution.

Slides are embedded in 10.5% Mowiol containing 2.5% DABCO as antifade agent. Cells are analysed by microscopy. This method is particularly useful for the detection of tenascin-W or any other protein produced by cells in culture to which an antibody is available and can be used to analyze substances that affect the synthesis or deposition of the respective antigens.

As is apparent to one of ordinary skill in the art, variations in the above-described methods can be introduced with ease to attain the same objective. Various incubating conditions, labels, apparatus and materials can be chosen according to individual preference. All publications referred to herein are incorporated by reference in their entirety as if each were referred to individually.

What is claimed is:

1. An isolated antibody that specifically recognizes amino acids 791-1054 of the polypeptide having the amino acid sequence shown in SEQ ID NO: 4.

2. The isolated antibody of claim 1, for the manufacture of a medicament.

3. The isolated antibody of claim 2, wherein said medicament is for the treatment of breast cancer.

4. An isolated antibody that specifically recognizes one or more of the three C-terminal fibronectin III repeats of mammalian tenascin W.

5. The isolated antibody of claim 4, wherein said antibody specifically recognizes one or more of the three C-terminal fibronectin III repeats in the region comprising amino acids 791-1054 of the tenascin W polypeptide having the amino acid sequence shown in SEQ ID NO: 4.

6. The isolated antibody of claim 5, for the manufacture of a medicament.

7. The isolated antibody of claim 6, wherein said medicament is for the treatment of breast cancer.

* * * * *

SEQUENCE LISTING

```
<160> NUMBER OF SEQ ID NOS: 28

<210> SEQ ID NO 1
<211> LENGTH: 3891
<212> TYPE: DNA
<213> ORGANISM: Mus musculus
<220> FEATURE:
<221> NAME/KEY: CDS
<222> LOCATION: (1)...(3891)
<223> OTHER INFORMATION: Mouse tenascin-W

<400> SEQUENCE: 1 atg ggt ctc tgg ggg atg ctc gcc ttc ccc ctg gga ttt ctg ctt gct        48
Met Gly Leu Trp Gly Met Leu Ala Phe Pro Leu Gly Phe Leu Leu Ala
 1               5                  10                  15 tct gtg ctc ctg gtg gct tcg gcc cca gcc act cca gag tct ccc ggc        96
Ser Val Leu Leu Val Ala Ser Ala Pro Ala Thr Pro Glu Ser Pro Gly
             20                  25                  30 tgc agc aac aaa gag caa cag gtc act gtt agc cac acc tac aag att       144
Cys Ser Asn Lys Glu Gln Gln Val Thr Val Ser His Thr Tyr Lys Ile
         35                  40                  45 gac gtg ccc aag tct gct ctg gtt caa gta gag acc gac cca cag tca       192
Asp Val Pro Lys Ser Ala Leu Val Gln Val Glu Thr Asp Pro Gln Ser
     50                  55                  60 ctc agc gat gat ggg aca tca ctc ttg gct ccc ggg gag gat ggg gag       240
Leu Ser Asp Asp Gly Thr Ser Leu Leu Ala Pro Gly Glu Asp Gly Glu
 65                  70                  75                  80 gag cag aac att atc ttc agg cac aac atc cgt ctt cag aca ccg cag       288
Glu Gln Asn Ile Ile Phe Arg His Asn Ile Arg Leu Gln Thr Pro Gln
                 85                  90                  95 aag aat tgc gac ctg gca gac agt gtc cag gac ctg cta gcc cgg atg       336
Lys Asn Cys Asp Leu Ala Asp Ser Val Gln Asp Leu Leu Ala Arg Met
            100                 105                 110 aaa aag ctg gag gaa gag atg gca gag ctg aag gag cag tgc aat acc       384
Lys Lys Leu Glu Glu Glu Met Ala Glu Leu Lys Glu Gln Cys Asn Thr
        115                 120                 125 aac cgc tgc tgc cag ggg gct gct gat ctg agc cgt cac tgc agt ggc       432
Asn Arg Cys Cys Gln Gly Ala Ala Asp Leu Ser Arg His Cys Ser Gly
    130                 135                 140 cac ggg acc ttc ctc cct gag acc tgc agc tgc cac tgt gac cag ggc       480
His Gly Thr Phe Leu Pro Glu Thr Cys Ser Cys His Cys Asp Gln Gly
145                 150                 155                 160 tgg gag ggc gca gac tgt gat cag ccc acc tgt cct ggg gct tgc aac       528
Trp Glu Gly Ala Asp Cys Asp Gln Pro Thr Cys Pro Gly Ala Cys Asn
                165                 170                 175 ggc cac ggg cgc tgt gtg gat ggg cag tgc gtg tgt gac gcg ccc tat       576
Gly His Gly Arg Cys Val Asp Gly Gln Cys Val Cys Asp Ala Pro Tyr
            180                 185                 190 gtg ggg gtc gac tgc gcc tac gcc gcc tgt ccc cag gac tgc agt ggg       624
Val Gly Val Asp Cys Ala Tyr Ala Ala Cys Pro Gln Asp Cys Ser Gly
        195                 200                 205 cat ggc gtg tgc gtg cag ggt gtc tgc cag tgc cac gag gac ttc aca       672
```

```
                His Gly Val Cys Val Gln Gly Val Cys Gln Cys His Glu Asp Phe Thr
                    210                 215                 220 gca gag gac tgc agc gag cag cgc tgt cct ggc gac tgt agt ggc aat          720
Ala Glu Asp Cys Ser Glu Gln Arg Cys Pro Gly Asp Cys Ser Gly Asn
225                 230                 235                 240 ggt ttc tgt gac act ggc gag tgt tac tgt gag atg ggc ttt act ggc          768
Gly Phe Cys Asp Thr Gly Glu Cys Tyr Cys Glu Met Gly Phe Thr Gly
                245                 250                 255 ccc gac tgt tcc cag gtg gtg gct cct cag ggc ctg cag ttg ctc aag          816
Pro Asp Cys Ser Gln Val Val Ala Pro Gln Gly Leu Gln Leu Leu Lys
            260                 265                 270 agc acg gag aac tct ctg ctg gtg agt tgg gag ccc tcc agt gag gta          864
Ser Thr Glu Asn Ser Leu Leu Val Ser Trp Glu Pro Ser Ser Glu Val
        275                 280                 285 gac tac tac ctg ctc agc tac tac ccc ctg ggg aag gag caa gct aca          912
Asp Tyr Tyr Leu Leu Ser Tyr Tyr Pro Leu Gly Lys Glu Gln Ala Thr
    290                 295                 300 aaa cag gtc cgg gta ccc aag gag cag cac acc tat gac atc acc ggc          960
Lys Gln Val Arg Val Pro Lys Glu Gln His Thr Tyr Asp Ile Thr Gly
305                 310                 315                 320 ttg ctg cct gga acc aag tac ata gtc acc ctg cgc aac gtg aag aaa         1008
Leu Leu Pro Gly Thr Lys Tyr Ile Val Thr Leu Arg Asn Val Lys Lys
                325                 330                 335 gac att tcc agc agc cct cag cat cta ctt gcc acc aca gac ctt gct         1056
Asp Ile Ser Ser Ser Pro Gln His Leu Leu Ala Thr Thr Asp Leu Ala
                340                 345                 350 gtg ctt ggc act gcc tgg gta aat gaa gag act gag aca tcc ctc gat         1104
Val Leu Gly Thr Ala Trp Val Asn Glu Glu Thr Glu Thr Ser Leu Asp
            355                 360                 365 gtg gag tgg gag aac cct ctg act gag gtg gac tat tac aag ctt cgg         1152
Val Glu Trp Glu Asn Pro Leu Thr Glu Val Asp Tyr Tyr Lys Leu Arg
        370                 375                 380 tat ggc ccc tta aca ggg cag gag gtg aca gag gtc act gtg ccc aag         1200
Tyr Gly Pro Leu Thr Gly Gln Glu Val Thr Glu Val Thr Val Pro Lys
385                 390                 395                 400 agc cgt gat ccc aag agc aga tat gac atc act ggt ctg cag cct gga         1248
Ser Arg Asp Pro Lys Ser Arg Tyr Asp Ile Thr Gly Leu Gln Pro Gly
                405                 410                 415 acg gaa tat aaa atc aca gtt gtg ccc atc cga ggt gat ctg gag gga         1296
Thr Glu Tyr Lys Ile Thr Val Val Pro Ile Arg Gly Asp Leu Glu Gly
                420                 425                 430 aag ccg att ctc ctg aat ggc agg aca gaa att gat gga cca acc aat         1344
Lys Pro Ile Leu Leu Asn Gly Arg Thr Glu Ile Asp Gly Pro Thr Asn
            435                 440                 445 gtg gtc aca aat cag gtg aca gaa gac aca gca tct gtt tcc tgg gat         1392
Val Val Thr Asn Gln Val Thr Glu Asp Thr Ala Ser Val Ser Trp Asp
        450                 455                 460 cca gtg agg gct gac ata gac aag tat gtg gtg cgc tat atc gcc ccc         1440
Pro Val Arg Ala Asp Ile Asp Lys Tyr Val Val Arg Tyr Ile Ala Pro
465                 470                 475                 480 gat ggg gag acc aag gag aag gca gta cca aag gac cag agc agc acc         1488
Asp Gly Glu Thr Lys Glu Lys Ala Val Pro Lys Asp Gln Ser Ser Thr
                485                 490                 495 gtt ctc aca ggc ctg aag cca gga gag gcc tac aaa gtc ttt gtg tgg         1536
Val Leu Thr Gly Leu Lys Pro Gly Glu Ala Tyr Lys Val Phe Val Trp
                500                 505                 510 gct gag agg ggc aac caa ggc agc aag aaa gca gac acc aag gcc ctc         1584
Ala Glu Arg Gly Asn Gln Gly Ser Lys Lys Ala Asp Thr Lys Ala Leu
            515                 520                 525
```

```
aca gaa att gac agt cca gaa aac ctg gtg act gac cgg gtg aca gag    1632
Thr Glu Ile Asp Ser Pro Glu Asn Leu Val Thr Asp Arg Val Thr Glu
    530                 535                 540 aac agc ctc tct gtc tcg tgg gac cca gtg gag gct gac atc gac agg    1680
Asn Ser Leu Ser Val Ser Trp Asp Pro Val Glu Ala Asp Ile Asp Arg
545                 550                 555                 560 tat gtg gta agc tac act tcc gtg gat gga gag acg aag cag gtt cca    1728
Tyr Val Val Ser Tyr Thr Ser Val Asp Gly Glu Thr Lys Gln Val Pro
                565                 570                 575 gtg aag aag gac cag agg agc acc gtc ctc acc ggc ctg agt ccc ggt    1776
Val Lys Lys Asp Gln Arg Ser Thr Val Leu Thr Gly Leu Ser Pro Gly
            580                 585                 590 gtg gag tac aaa gtt tac gtg tgg gca gag aaa ggc gat cgg gag agc    1824
Val Glu Tyr Lys Val Tyr Val Trp Ala Glu Lys Gly Asp Arg Glu Ser
        595                 600                 605 aag aag gcc aac acc aag gct ccc aca gac atc gac agc ccc aaa aac    1872
Lys Lys Ala Asn Thr Lys Ala Pro Thr Asp Ile Asp Ser Pro Lys Asn
    610                 615                 620 ttg gta act gac cag gtg aca gag aac act ctc agt gtc tcc tgg gac    1920
Leu Val Thr Asp Gln Val Thr Glu Asn Thr Leu Ser Val Ser Trp Asp
625                 630                 635                 640 cct gtt cag gcc aac att gac agg tat atg gtg agc tac acc tct gcc    1968
Pro Val Gln Ala Asn Ile Asp Arg Tyr Met Val Ser Tyr Thr Ser Ala
                645                 650                 655 gat gga gag aca aga gag gtc cca gtg cct aag gag aag agc agt acc    2016
Asp Gly Glu Thr Arg Glu Val Pro Val Pro Lys Glu Lys Ser Ser Thr
            660                 665                 670 gtc ctg act ggc ctg agg cca ggt gtg gag tac aag gtc cat gtg tgg    2064
Val Leu Thr Gly Leu Arg Pro Gly Val Glu Tyr Lys Val His Val Trp
        675                 680                 685 gcc cag aag ggg acc cag gag agc aga aag gcc aac acc aag gcc ccc    2112
Ala Gln Lys Gly Thr Gln Glu Ser Arg Lys Ala Asn Thr Lys Ala Pro
    690                 695                 700 aca gat att gat ggc ccc aaa aac ctg gtg act gac cag gtg acc gag    2160
Thr Asp Ile Asp Gly Pro Lys Asn Leu Val Thr Asp Gln Val Thr Glu
705                 710                 715                 720 acc act ctt agt gtc tcc tgg gac cca gtg gag gct gac att gat agg    2208
Thr Thr Leu Ser Val Ser Trp Asp Pro Val Glu Ala Asp Ile Asp Arg
                725                 730                 735 tac atg gtt cgc tac acg tct cct gat gga gag acc aag gag gtg cct    2256
Tyr Met Val Arg Tyr Thr Ser Pro Asp Gly Glu Thr Lys Glu Val Pro
            740                 745                 750 gtg tca aag gat aag agc agc aca gtc ctg agg ggc ctg agg cca ggt    2304
Val Ser Lys Asp Lys Ser Ser Thr Val Leu Arg Gly Leu Arg Pro Gly
        755                 760                 765 gtg gag tac aag gtg gat gta tgg gcc cag aag ggg gcc cag gac agc    2352
Val Glu Tyr Lys Val Asp Val Trp Ala Gln Lys Gly Ala Gln Asp Ser
    770                 775                 780 cgg aag gcc aac acc aag gcc ccc aca gat att gac agc cct aaa aac    2400
Arg Lys Ala Asn Thr Lys Ala Pro Thr Asp Ile Asp Ser Pro Lys Asn
785                 790                 795                 800 cta gtg act gag cag gtg gca gag agc act gcc acc gtg tcc tgg gac    2448
Leu Val Thr Glu Gln Val Ala Glu Ser Thr Ala Thr Val Ser Trp Asp
                805                 810                 815 cca gta gag gct gac atc gac agg tat gtg gtg cgc tac acc tct gct    2496
Pro Val Glu Ala Asp Ile Asp Arg Tyr Val Val Arg Tyr Thr Ser Ala
            820                 825                 830 gat gga gag acc agg gag att cca gtg agg aag gag aag agc agc act    2544
Asp Gly Glu Thr Arg Glu Ile Pro Val Arg Lys Glu Lys Ser Ser Thr
    835                 840                 845
```

```
gtc ctc aca ggc ctg aga ccg ggt gtg gag tac acg gtc caa gtg tgg       2592
Val Leu Thr Gly Leu Arg Pro Gly Val Glu Tyr Thr Val Gln Val Trp
    850                 855                 860 gct cag aag ggg gcc cgg gag agc aag aag gcc aaa acc aag gcc ccc       2640
Ala Gln Lys Gly Ala Arg Glu Ser Lys Lys Ala Lys Thr Lys Ala Pro
865                 870                 875                 880 aca gaa att gac agc ccc aag aac ttg gtg acc aac cga gtc aca gaa       2688
Thr Glu Ile Asp Ser Pro Lys Asn Leu Val Thr Asn Arg Val Thr Glu
                885                 890                 895 aat aca gcc acc atc tcc tgg gac cca gtg cga gcc aac att gac agg       2736
Asn Thr Ala Thr Ile Ser Trp Asp Pro Val Arg Ala Asn Ile Asp Arg
            900                 905                 910 tac atg gtt cgc tac acc tct gcg gat gga gag act aag gag att cca       2784
Tyr Met Val Arg Tyr Thr Ser Ala Asp Gly Glu Thr Lys Glu Ile Pro
        915                 920                 925 gtg tca aag gat cag agt aac acc atc ctg aca ggc ctg aaa cca ggc       2832
Val Ser Lys Asp Gln Ser Asn Thr Ile Leu Thr Gly Leu Lys Pro Gly
    930                 935                 940 atg gaa tat acc att cat gtg tgg gcc cag aag ggg gcc cgg gag agc       2880
Met Glu Tyr Thr Ile His Val Trp Ala Gln Lys Gly Ala Arg Glu Ser
945                 950                 955                 960 aag aag gct gat acc aag gcc cta aca gaa att gac cct ccc aga aat       2928
Lys Lys Ala Asp Thr Lys Ala Leu Thr Glu Ile Asp Pro Pro Arg Asn
                965                 970                 975 ctc cgt ccg ttc ggg gta aca cat tct ggt ggg gtt ttg acc tgg ttg       2976
Leu Arg Pro Phe Gly Val Thr His Ser Gly Gly Val Leu Thr Trp Leu
            980                 985                 990 ccc cca tct gct caa att gat ggc tac att ttg acc tac cag ttc cca       3024
Pro Pro Ser Ala Gln Ile Asp Gly Tyr Ile Leu Thr Tyr Gln Phe Pro
        995                 1000                1005 aat ggc acc gtg aag ggg gtg gag ctc cca aga ggc cag cag aga ttt       3072
Asn Gly Thr Val Lys Gly Val Glu Leu Pro Arg Gly Gln Gln Arg Phe
    1010                1015                1020 gaa ttg caa gac ctg gaa cag ggt gtc acc tat cct gtt tcc ttg gtt       3120
Glu Leu Gln Asp Leu Glu Gln Gly Val Thr Tyr Pro Val Ser Leu Val
1025                1030                1035                1040 gcc ttc aaa ggt aat cag cgg agc cgg act gtg tct acc acc ctt tct       3168
Ala Phe Lys Gly Asn Gln Arg Ser Arg Thr Val Ser Thr Thr Leu Ser
                1045                1050                1055 aca gtg gat gct cgc ttt cca cac ccc tca gac tgc agt caa gtt cag       3216
Thr Val Asp Ala Arg Phe Pro His Pro Ser Asp Cys Ser Gln Val Gln
            1060                1065                1070 cag aac acc aac gct gcc agt ggg ctc tac acc atc tac ctc aat ggt       3264
Gln Asn Thr Asn Ala Ala Ser Gly Leu Tyr Thr Ile Tyr Leu Asn Gly
        1075                1080                1085 gat gcc agc cgg ccc atg cag gtg tac tgc gac atg gac act gac gga       3312
Asp Ala Ser Arg Pro Met Gln Val Tyr Cys Asp Met Asp Thr Asp Gly
    1090                1095                1100 ggc ggc tgg att gtc ttc cag aga cgg aac act ggg cag ctg gat ttc       3360
Gly Gly Trp Ile Val Phe Gln Arg Arg Asn Thr Gly Gln Leu Asp Phe
1105                1110                1115                1120 ttc aag cgt tgg cgg agt tat gta gaa ggt ttt ggg gac ccc atg aag       3408
Phe Lys Arg Trp Arg Ser Tyr Val Glu Gly Phe Gly Asp Pro Met Lys
                1125                1130                1135 gag ttc tgg ctt gga ctt gat aaa cta cat aat ctc acc act ggc acc       3456
Glu Phe Trp Leu Gly Leu Asp Lys Leu His Asn Leu Thr Thr Gly Thr
            1140                1145                1150 acc act cgg tat gag gtg agg gca gac tta cag act ttc aat gaa tct       3504
Thr Thr Arg Tyr Glu Val Arg Ala Asp Leu Gln Thr Phe Asn Glu Ser
```

-continued

```
                  1155                1160                1165
gcc tac gct gta tat gat ttc ttc caa gtg gca tcc agc aaa gag cgg    3552
Ala Tyr Ala Val Tyr Asp Phe Phe Gln Val Ala Ser Ser Lys Glu Arg
    1170                1175                1180 tac aag ctg tcg gtt ggg aaa tac aga ggc aca gcc ggg gat gct ctc    3600
Tyr Lys Leu Ser Val Gly Lys Tyr Arg Gly Thr Ala Gly Asp Ala Leu
1185                1190                1195                1200 acc tac cac aat gga tgg aag ttc acg act ttt gac aga gac agt gat    3648
Thr Tyr His Asn Gly Trp Lys Phe Thr Thr Phe Asp Arg Asp Ser Asp
            1205                1210                1215 att gcc ctc agc aac tgt gca ctg acg cat cat ggt ggc tgg tgg tat    3696
Ile Ala Leu Ser Asn Cys Ala Leu Thr His His Gly Gly Trp Trp Tyr
        1220                1225                1230 aag aac tgc cat ttg gcc aac ccg aat ggc aaa tat ggg gag acc aag    3744
Lys Asn Cys His Leu Ala Asn Pro Asn Gly Lys Tyr Gly Glu Thr Lys
    1235                1240                1245 cac agc gag ggg gtg aac tgg gag cca tgg aag gga cat gag ttc tcc    3792
His Ser Glu Gly Val Asn Trp Glu Pro Trp Lys Gly His Glu Phe Ser
    1250                1255                1260 att cct tat gtg gag ctg aaa atc cgc ccg ttt ggt tac agc aga gac    3840
Ile Pro Tyr Val Glu Leu Lys Ile Arg Pro Phe Gly Tyr Ser Arg Asp
1265                1270                1275                1280 cgt ttc tct ggc aga aag aag cgc tcc ata gga aaa gca agg atg ttc    3888
Arg Phe Ser Gly Arg Lys Lys Arg Ser Ile Gly Lys Ala Arg Met Phe
            1285                1290                1295 tga                                                                 3891
*

<210> SEQ ID NO 2
<211> LENGTH: 1296
<212> TYPE: PRT
<213> ORGANISM: Mus musculus

<400> SEQUENCE: 2

Met Gly Leu Trp Gly Met Leu Ala Phe Pro Leu Gly Phe Leu Leu Ala
 1               5                  10                  15

Ser Val Leu Leu Val Ala Ser Ala Pro Ala Thr Pro Glu Ser Pro Gly
            20                  25                  30

Cys Ser Asn Lys Glu Gln Gln Val Thr Val Ser His Thr Tyr Lys Ile
        35                  40                  45

Asp Val Pro Lys Ser Ala Leu Val Gln Val Glu Thr Asp Pro Gln Ser
    50                  55                  60

Leu Ser Asp Asp Gly Thr Ser Leu Leu Ala Pro Gly Glu Asp Gly Glu
65                  70                  75                  80

Glu Gln Asn Ile Ile Phe Arg His Asn Ile Arg Leu Gln Thr Pro Gln
                85                  90                  95

Lys Asn Cys Asp Leu Ala Asp Ser Val Gln Asp Leu Leu Ala Arg Met
            100                 105                 110

Lys Lys Leu Glu Glu Glu Met Ala Glu Leu Lys Glu Gln Cys Asn Thr
        115                 120                 125

Asn Arg Cys Cys Gln Gly Ala Ala Asp Leu Ser Arg His Cys Ser Gly
    130                 135                 140

His Gly Thr Phe Leu Pro Glu Thr Cys Ser Cys His Cys Asp Gln Gly
145                 150                 155                 160

Trp Glu Gly Ala Asp Cys Asp Gln Pro Thr Cys Pro Gly Ala Cys Asn
                165                 170                 175

Gly His Gly Arg Cys Val Asp Gly Gln Cys Val Cys Asp Ala Pro Tyr
```

-continued

```
                180                 185                 190
Val Gly Val Asp Cys Ala Tyr Ala Cys Pro Gln Asp Cys Ser Gly
            195                 200                 205

His Gly Val Cys Val Gln Gly Val Cys Gln Cys His Glu Asp Phe Thr
210                 215                 220

Ala Glu Asp Cys Ser Glu Gln Arg Cys Pro Gly Asp Cys Ser Gly Asn
225                 230                 235                 240

Gly Phe Cys Asp Thr Gly Glu Cys Tyr Cys Glu Met Gly Phe Thr Gly
                245                 250                 255

Pro Asp Cys Ser Gln Val Val Ala Pro Gln Gly Leu Gln Leu Leu Lys
            260                 265                 270

Ser Thr Glu Asn Ser Leu Leu Val Ser Trp Glu Pro Ser Ser Glu Val
        275                 280                 285

Asp Tyr Tyr Leu Leu Ser Tyr Tyr Pro Leu Gly Lys Glu Gln Ala Thr
    290                 295                 300

Lys Gln Val Arg Val Pro Lys Glu Gln His Thr Tyr Asp Ile Thr Gly
305                 310                 315                 320

Leu Leu Pro Gly Thr Lys Tyr Ile Val Thr Leu Arg Asn Val Lys Lys
                325                 330                 335

Asp Ile Ser Ser Ser Pro Gln His Leu Leu Ala Thr Thr Asp Leu Ala
            340                 345                 350

Val Leu Gly Thr Ala Trp Val Asn Glu Glu Thr Glu Thr Ser Leu Asp
        355                 360                 365

Val Glu Trp Glu Asn Pro Leu Thr Glu Val Asp Tyr Tyr Lys Leu Arg
    370                 375                 380

Tyr Gly Pro Leu Thr Gly Gln Glu Val Thr Glu Val Thr Val Pro Lys
385                 390                 395                 400

Ser Arg Asp Pro Lys Ser Arg Tyr Asp Ile Thr Gly Leu Gln Pro Gly
                405                 410                 415

Thr Glu Tyr Lys Ile Thr Val Val Pro Ile Arg Gly Asp Leu Glu Gly
            420                 425                 430

Lys Pro Ile Leu Leu Asn Gly Arg Thr Glu Ile Asp Gly Pro Thr Asn
        435                 440                 445

Val Val Thr Asn Gln Val Thr Glu Asp Thr Ala Ser Val Ser Trp Asp
    450                 455                 460

Pro Val Arg Ala Asp Ile Asp Lys Tyr Val Val Arg Tyr Ile Ala Pro
465                 470                 475                 480

Asp Gly Glu Thr Lys Glu Lys Ala Val Pro Lys Asp Gln Ser Ser Thr
                485                 490                 495

Val Leu Thr Gly Leu Lys Pro Gly Glu Ala Tyr Lys Val Phe Val Trp
            500                 505                 510

Ala Glu Arg Gly Asn Gln Gly Ser Lys Lys Ala Asp Thr Lys Ala Leu
        515                 520                 525

Thr Glu Ile Asp Ser Pro Glu Asn Leu Val Thr Asp Arg Val Thr Glu
    530                 535                 540

Asn Ser Leu Ser Val Ser Trp Asp Pro Val Glu Ala Asp Ile Asp Arg
545                 550                 555                 560

Tyr Val Val Ser Tyr Thr Ser Val Asp Gly Glu Thr Lys Gln Val Pro
                565                 570                 575

Val Lys Lys Asp Gln Arg Ser Thr Val Leu Thr Gly Leu Ser Pro Gly
            580                 585                 590

Val Glu Tyr Lys Val Tyr Val Trp Ala Glu Lys Gly Asp Arg Glu Ser
        595                 600                 605
```

```
Lys Lys Ala Asn Thr Lys Ala Pro Thr Asp Ile Asp Ser Pro Lys Asn
    610                 615                 620

Leu Val Thr Asp Gln Val Thr Glu Asn Thr Leu Ser Val Ser Trp Asp
625                 630                 635                 640

Pro Val Gln Ala Asn Ile Asp Arg Tyr Met Val Ser Tyr Thr Ser Ala
                645                 650                 655

Asp Gly Glu Thr Arg Glu Val Pro Val Pro Lys Glu Lys Ser Ser Thr
            660                 665                 670

Val Leu Thr Gly Leu Arg Pro Gly Val Glu Tyr Lys Val His Val Trp
        675                 680                 685

Ala Gln Lys Gly Thr Gln Glu Ser Arg Lys Ala Asn Thr Lys Ala Pro
690                 695                 700

Thr Asp Ile Asp Gly Pro Lys Asn Leu Val Thr Asp Gln Val Thr Glu
705                 710                 715                 720

Thr Thr Leu Ser Val Ser Trp Asp Pro Val Glu Ala Asp Ile Asp Arg
                725                 730                 735

Tyr Met Val Arg Tyr Thr Ser Pro Asp Gly Glu Thr Lys Glu Val Pro
            740                 745                 750

Val Ser Lys Asp Lys Ser Ser Thr Val Leu Arg Gly Leu Arg Pro Gly
        755                 760                 765

Val Glu Tyr Lys Val Asp Val Trp Ala Gln Lys Gly Ala Gln Asp Ser
770                 775                 780

Arg Lys Ala Asn Thr Lys Ala Pro Thr Asp Ile Asp Ser Pro Lys Asn
785                 790                 795                 800

Leu Val Thr Glu Gln Val Ala Glu Ser Thr Ala Thr Val Ser Trp Asp
                805                 810                 815

Pro Val Glu Ala Asp Ile Asp Arg Tyr Val Val Arg Tyr Thr Ser Ala
            820                 825                 830

Asp Gly Glu Thr Arg Glu Ile Pro Val Arg Lys Glu Lys Ser Ser Thr
        835                 840                 845

Val Leu Thr Gly Leu Arg Pro Gly Val Glu Tyr Thr Val Gln Val Trp
850                 855                 860

Ala Gln Lys Gly Ala Arg Glu Ser Lys Lys Ala Lys Thr Lys Ala Pro
865                 870                 875                 880

Thr Glu Ile Asp Ser Pro Lys Asn Leu Val Thr Asn Arg Val Thr Glu
                885                 890                 895

Asn Thr Ala Thr Ile Ser Trp Asp Pro Val Arg Ala Asn Ile Asp Arg
            900                 905                 910

Tyr Met Val Arg Tyr Thr Ser Ala Asp Gly Glu Thr Lys Glu Ile Pro
        915                 920                 925

Val Ser Lys Asp Gln Ser Asn Thr Ile Leu Thr Gly Leu Lys Pro Gly
930                 935                 940

Met Glu Tyr Thr Ile His Val Trp Ala Gln Lys Gly Ala Arg Glu Ser
945                 950                 955                 960

Lys Lys Ala Asp Thr Lys Ala Leu Thr Glu Ile Asp Pro Pro Arg Asn
                965                 970                 975

Leu Arg Pro Phe Gly Val Thr His Ser Gly Val Leu Thr Trp Leu
            980                 985                 990

Pro Pro Ser Ala Gln Ile Asp Gly Tyr Ile Leu Thr Tyr Gln Phe Pro
        995                 1000                1005

Asn Gly Thr Val Lys Gly Val Glu Leu Pro Arg Gly Gln Gln Arg Phe
1010                1015                1020
```

```
Glu Leu Gln Asp Leu Glu Gln Gly Val Thr Tyr Pro Val Ser Leu Val
1025                1030                1035                1040

Ala Phe Lys Gly Asn Gln Arg Ser Arg Thr Val Ser Thr Thr Leu Ser
            1045                1050                1055

Thr Val Asp Ala Arg Phe Pro His Pro Ser Asp Cys Ser Gln Val Gln
        1060                1065                1070

Gln Asn Thr Asn Ala Ala Ser Gly Leu Tyr Thr Ile Tyr Leu Asn Gly
    1075                1080                1085

Asp Ala Ser Arg Pro Met Gln Val Tyr Cys Asp Met Asp Thr Asp Gly
1090                1095                1100

Gly Gly Trp Ile Val Phe Gln Arg Arg Asn Thr Gly Gln Leu Asp Phe
1105                1110                1115                1120

Phe Lys Arg Trp Arg Ser Tyr Val Glu Gly Phe Gly Asp Pro Met Lys
            1125                1130                1135

Glu Phe Trp Leu Gly Leu Asp Lys Leu His Asn Leu Thr Thr Gly Thr
        1140                1145                1150

Thr Thr Arg Tyr Glu Val Arg Ala Asp Leu Gln Thr Phe Asn Glu Ser
    1155                1160                1165

Ala Tyr Ala Val Tyr Asp Phe Phe Gln Val Ala Ser Ser Lys Glu Arg
1170                1175                1180

Tyr Lys Leu Ser Val Gly Lys Tyr Arg Gly Thr Ala Gly Asp Ala Leu
1185                1190                1195                1200

Thr Tyr His Asn Gly Trp Lys Phe Thr Thr Phe Asp Arg Asp Ser Asp
        1205                1210                1215

Ile Ala Leu Ser Asn Cys Ala Leu Thr His Gly Gly Trp Trp Tyr
    1220                1225                1230

Lys Asn Cys His Leu Ala Asn Pro Asn Gly Lys Tyr Gly Glu Thr Lys
    1235                1240                1245

His Ser Glu Gly Val Asn Trp Glu Pro Trp Lys Gly His Glu Phe Ser
    1250                1255                1260

Ile Pro Tyr Val Glu Leu Lys Ile Arg Pro Phe Gly Tyr Ser Arg Asp
1265                1270                1275                1280

Arg Phe Ser Gly Arg Lys Lys Arg Ser Ile Gly Lys Ala Arg Met Phe
            1285                1290                1295

<210> SEQ ID NO 3
<211> LENGTH: 3885
<212> TYPE: DNA
<213> ORGANISM: Homo sapiens
<220> FEATURE:
<221> NAME/KEY: CDS
<222> LOCATION: (1)...(3885)
<223> OTHER INFORMATION: Human tenascin-W

<400> SEQUENCE: 3 atg ttc cgc ttc cct atg ggg ctc ctg ctt ggc tct gtg ctc ctg gtg     48
Met Phe Arg Phe Pro Met Gly Leu Leu Leu Gly Ser Val Leu Leu Val
 1               5                  10                  15 gct tcg gcc cca gcc act ctg gag cct ccc ggc tgc agc aac aag gag     96
Ala Ser Ala Pro Ala Thr Leu Glu Pro Pro Gly Cys Ser Asn Lys Glu
             20                  25                  30 caa cag gtc act gtc agc cac acc tac aag atc gat gtg ccc aag tct    144
Gln Gln Val Thr Val Ser His Thr Tyr Lys Ile Asp Val Pro Lys Ser
         35                  40                  45 gcc ttg gtt cag gtt gac gct gac cct cag ccc ctc agt gac gat ggg    192
Ala Leu Val Gln Val Asp Ala Asp Pro Gln Pro Leu Ser Asp Asp Gly
     50                  55                  60
```

-continued

| | |
|---|---|
| gct tcg ctc ttg gcc ctg ggg gag gcc agg gag gaa cag aac atc atc<br>Ala Ser Leu Leu Ala Leu Gly Glu Ala Arg Glu Glu Gln Asn Ile Ile<br>65                    70                    75                    80 | 240 |
| ttc agg cac aac atc cgc ctt cag acg cca cag aag gac tgc gag ttg<br>Phe Arg His Asn Ile Arg Leu Gln Thr Pro Gln Lys Asp Cys Glu Leu<br>                  85                    90                    95 | 288 |
| gca ggc agt gtc cag gac ctc ctg gcc cgg gtg aag aag ctg gag gaa<br>Ala Gly Ser Val Gln Asp Leu Leu Ala Arg Val Lys Lys Leu Glu Glu<br>                  100                 105              110 | 336 |
| gag atg gtg gag atg aag gaa cag tgt agt gcc cag cgc tgc tgc cag<br>Glu Met Val Glu Met Lys Glu Gln Cys Ser Ala Gln Arg Cys Cys Gln<br>115                    120                 125 | 384 |
| gga gtc act gat cta agc cgc cac tgc agc ggc cac ggg acc ttc tcc<br>Gly Val Thr Asp Leu Ser Arg His Cys Ser Gly His Gly Thr Phe Ser<br>130                    135                 140 | 432 |
| ctg gag acc tgc agc tgc cac tgc gaa gag ggc agg gag ggc ccc gcc<br>Leu Glu Thr Cys Ser Cys His Cys Glu Glu Gly Arg Glu Gly Pro Ala<br>145                    150                 155              160 | 480 |
| tgc gag cgg ctg gcc tgc ccc ggg gcg tgc agc ggc cac ggg cgt tgc<br>Cys Glu Arg Leu Ala Cys Pro Gly Ala Cys Ser Gly His Gly Arg Cys<br>                  165                 170              175 | 528 |
| gtg gac ggg cgc tgc ctg tgc cat gag ccc tac gtg ggt gcc gac tgc<br>Val Asp Gly Arg Cys Leu Cys His Glu Pro Tyr Val Gly Ala Asp Cys<br>180                    185                 190 | 576 |
| ggc tac ccg gcc tgc cct gag aac tgc agc gga cac ggc gag tgc gtg<br>Gly Tyr Pro Ala Cys Pro Glu Asn Cys Ser Gly His Gly Glu Cys Val<br>                  195                 200              205 | 624 |
| cgc ggc gtg tgc cag tgc cac gaa gac ttc atg tcg gag gac tgc agc<br>Arg Gly Val Cys Gln Cys His Glu Asp Phe Met Ser Glu Asp Cys Ser<br>210                    215                 220 | 672 |
| gag aag cgc tgt ccc ggc gac tgc agc ggc cac ggc ttc tgt gac acg<br>Glu Lys Arg Cys Pro Gly Asp Cys Ser Gly His Gly Phe Cys Asp Thr<br>225                    230                 235              240 | 720 |
| ggc gag tgc tac tgc gag gag ggc ttc aca ggc ctg gac tgt gcc cag<br>Gly Glu Cys Tyr Cys Glu Glu Gly Phe Thr Gly Leu Asp Cys Ala Gln<br>                  245                 250              255 | 768 |
| gtg gtc acc cca cag ggc ctg cag ctg ctc aag aac acg gag gat tct<br>Val Val Thr Pro Gln Gly Leu Gln Leu Leu Lys Asn Thr Glu Asp Ser<br>260                    265                 270 | 816 |
| ctg ctg gtg agc tgg gag ccc tcc agc cag gtg gat cac tac ctc ctc<br>Leu Leu Val Ser Trp Glu Pro Ser Ser Gln Val Asp His Tyr Leu Leu<br>                  275                 280              285 | 864 |
| agc tac tac ccc ctg ggg aag gag ctc tct ggg aag cag atc caa gtg<br>Ser Tyr Tyr Pro Leu Gly Lys Glu Leu Ser Gly Lys Gln Ile Gln Val<br>290                    295                 300 | 912 |
| ccc aag gag cag cac agc tat gag att ctt ggt ttg ctg cct gga acc<br>Pro Lys Glu Gln His Ser Tyr Glu Ile Leu Gly Leu Leu Pro Gly Thr<br>305                    310                 315              320 | 960 |
| aag tac ata gtc acc ctg cgt aac gtc aag aat gaa gtt tct agc agc<br>Lys Tyr Ile Val Thr Leu Arg Asn Val Lys Asn Glu Val Ser Ser Ser<br>                  325                 330              335 | 1008 |
| cca cag cat cta ctt gcc acc aca gac ctt gct gtg ctt ggc act gcc<br>Pro Gln His Leu Leu Ala Thr Thr Asp Leu Ala Val Leu Gly Thr Ala<br>340                    345                 350 | 1056 |
| tgg gtg aca gat gag act gag aac tcc ctt gac gtg gag tgg gaa aac<br>Trp Val Thr Asp Glu Thr Glu Asn Ser Leu Asp Val Glu Trp Glu Asn<br>355                    360                 365 | 1104 |
| ccc tca act gag gtg gac tac tac aag ctg cga tat ggc ccc atg aca<br>Pro Ser Thr Glu Val Asp Tyr Tyr Lys Leu Arg Tyr Gly Pro Met Thr<br>370                    375                 380 | 1152 |

```
gga cag gag gta gct gag gtc act gtg ccc aag agc agt gac ccc aag    1200
Gly Gln Glu Val Ala Glu Val Thr Val Pro Lys Ser Ser Asp Pro Lys
385                 390                 395                 400 agc cga tat gac atc act ggt ctg cac ccg ggg act gag tat aag atc    1248
Ser Arg Tyr Asp Ile Thr Gly Leu His Pro Gly Thr Glu Tyr Lys Ile
                405                 410                 415 acg gtg gtg ccc atg aga gga gag ctg gag ggc aag ccg atc ctc ctg    1296
Thr Val Val Pro Met Arg Gly Glu Leu Glu Gly Lys Pro Ile Leu Leu
            420                 425                 430 aat ggc agg aca gaa att gac agt cca acc aat gtt gtc act gat cga    1344
Asn Gly Arg Thr Glu Ile Asp Ser Pro Thr Asn Val Val Thr Asp Arg
        435                 440                 445 gtg act gaa gac aca gca act gtc tcc tgg gac cca gtg cag gct gtc    1392
Val Thr Glu Asp Thr Ala Thr Val Ser Trp Asp Pro Val Gln Ala Val
    450                 455                 460 ata gac aag tat gta gtg cgc tac act tct gct gat ggg gac acc aag    1440
Ile Asp Lys Tyr Val Val Arg Tyr Thr Ser Ala Asp Gly Asp Thr Lys
465                 470                 475                 480 gaa atg gca gtg cac aag gat gag agc agc act gtc ctg acg ggc ctg    1488
Glu Met Ala Val His Lys Asp Glu Ser Ser Thr Val Leu Thr Gly Leu
                485                 490                 495 aag cca gga gag gca tac aag gtc tac gtg tgg gct gaa agg ggc aac    1536
Lys Pro Gly Glu Ala Tyr Lys Val Tyr Val Trp Ala Glu Arg Gly Asn
            500                 505                 510 cag ggg agc aag aaa gct gac acc aat gcc ctc aca gaa att gac agc    1584
Gln Gly Ser Lys Lys Ala Asp Thr Asn Ala Leu Thr Glu Ile Asp Ser
        515                 520                 525 cca gca aac ctg gtg act gac cgg gtg act gag aat acc gcc acc atc    1632
Pro Ala Asn Leu Val Thr Asp Arg Val Thr Glu Asn Thr Ala Thr Ile
    530                 535                 540 tcc tgg gac ccg gta cag gcc acc att gac aag tac gtg gtg cgc tac    1680
Ser Trp Asp Pro Val Gln Ala Thr Ile Asp Lys Tyr Val Val Arg Tyr
545                 550                 555                 560 acc tct gct gac gac caa gag acc aga gag gtt ctg gtg ggg aag gag    1728
Thr Ser Ala Asp Asp Gln Glu Thr Arg Glu Val Leu Val Gly Lys Glu
                565                 570                 575 cag agc agc act gtc ctg aca ggc ctg agg cca ggt gtg gag tac aca    1776
Gln Ser Ser Thr Val Leu Thr Gly Leu Arg Pro Gly Val Glu Tyr Thr
            580                 585                 590 gtg cat gtc tgg gcc cag aag ggg gac cga gag agc aag aag gct gac    1824
Val His Val Trp Ala Gln Lys Gly Asp Arg Glu Ser Lys Lys Ala Asp
        595                 600                 605 acc aac gcc ccg aca gat att gac agc ccc aaa aac ctg gtg act gac    1872
Thr Asn Ala Pro Thr Asp Ile Asp Ser Pro Lys Asn Leu Val Thr Asp
    610                 615                 620 cgg gtg aca gag aat atg gcc acg gtc tcc tgg gac ccg gtg cag gcc    1920
Arg Val Thr Glu Asn Met Ala Thr Val Ser Trp Asp Pro Val Gln Ala
625                 630                 635                 640 gcc att gac aag tac gtg gtg cgc tac acc tct gct ggt gga gag acc    1968
Ala Ile Asp Lys Tyr Val Val Arg Tyr Thr Ser Ala Gly Gly Glu Thr
                645                 650                 655 agg gag gtt ccg gtg ggg aag gag cag agc agc aca gtc ctg aca ggc    2016
Arg Glu Val Pro Val Gly Lys Glu Gln Ser Ser Thr Val Leu Thr Gly
            660                 665                 670 ctg aga ccg ggt atg gag tac atg gtg cac gtg tgg gcc cag aag ggg    2064
Leu Arg Pro Gly Met Glu Tyr Met Val His Val Trp Ala Gln Lys Gly
        675                 680                 685 gac cag gag agc aag aag gcc gac acc aag gcc cag aca gac att gac    2112
Asp Gln Glu Ser Lys Lys Ala Asp Thr Lys Ala Gln Thr Asp Ile Asp
```

-continued

```
                  690                 695                 700
agc ccc caa aac ctg gtg acc gac cgg gtg aca gag aat atg gcc act        2160
Ser Pro Gln Asn Leu Val Thr Asp Arg Val Thr Glu Asn Met Ala Thr
705                 710                 715                 720 gtc tcc tgg gac ccg gtg cgg gcc acc att gac agg tat gtg gtg cgc        2208
Val Ser Trp Asp Pro Val Arg Ala Thr Ile Asp Arg Tyr Val Val Arg
            725                 730                 735 tac acc tct gcc aag gac gga gag acc agg gag gtt ccg gtg ggg aag        2256
Tyr Thr Ser Ala Lys Asp Gly Glu Thr Arg Glu Val Pro Val Gly Lys
        740                 745                 750 gag cag agt agc act gtc ctg acg ggc ctg agg ccg ggt gtg gag tac        2304
Glu Gln Ser Ser Thr Val Leu Thr Gly Leu Arg Pro Gly Val Glu Tyr
    755                 760                 765 acg gtg cac gtg tgg gcc cag aag ggg gcc cag gag agc aag aag gct        2352
Thr Val His Val Trp Ala Gln Lys Gly Ala Gln Glu Ser Lys Lys Ala
770                 775                 780 gac acc aag gcc cag aca gac att gac agc ccc caa aac ctg gtc act        2400
Asp Thr Lys Ala Gln Thr Asp Ile Asp Ser Pro Gln Asn Leu Val Thr
785                 790                 795                 800 gac tgg gtg aca gag aat aca gcc act gtc tcc tgg gac ccg gtg cag        2448
Asp Trp Val Thr Glu Asn Thr Ala Thr Val Ser Trp Asp Pro Val Gln
            805                 810                 815 gcc acc att gac agg tat gtg gtg cac tac acg tct gcc aac gga gag        2496
Ala Thr Ile Asp Arg Tyr Val Val His Tyr Thr Ser Ala Asn Gly Glu
        820                 825                 830 acc agg gag gtt cca gtg ggg aag gag cag agc agc act gtc ctg acg        2544
Thr Arg Glu Val Pro Val Gly Lys Glu Gln Ser Ser Thr Val Leu Thr
    835                 840                 845 ggc ctg agg ccg ggc atg gag tac acg gtg cac gtg tgg gcc cag aag        2592
Gly Leu Arg Pro Gly Met Glu Tyr Thr Val His Val Trp Ala Gln Lys
850                 855                 860 ggg aac cag gag agc aag aag gct gac acc aag gcc cag aca gaa att        2640
Gly Asn Gln Glu Ser Lys Lys Ala Asp Thr Lys Ala Gln Thr Glu Ile
865                 870                 875                 880 gac ggc ccc aaa aac cta gtg act gac tgg gtg acg gag aat atg gcc        2688
Asp Gly Pro Lys Asn Leu Val Thr Asp Trp Val Thr Glu Asn Met Ala
            885                 890                 895 act gtc tcc tgg gac ccg gtt cag gcc acc att gac aag tac atg gtg        2736
Thr Val Ser Trp Asp Pro Val Gln Ala Thr Ile Asp Lys Tyr Met Val
        900                 905                 910 cgc tac acc tct gct gac gga gag acc agg gag gtt ccg gtg ggg aag        2784
Arg Tyr Thr Ser Ala Asp Gly Glu Thr Arg Glu Val Pro Val Gly Lys
    915                 920                 925 gag cac agc agc act gtc ctg acg ggc ctg aga cca ggc atg gag tac        2832
Glu His Ser Ser Thr Val Leu Thr Gly Leu Arg Pro Gly Met Glu Tyr
930                 935                 940 atg gtg cac gtg tgg gcc cag aag ggg gcc cag gag agc aag aag gct        2880
Met Val His Val Trp Ala Gln Lys Gly Ala Gln Glu Ser Lys Lys Ala
945                 950                 955                 960 gac acc aag gcc cag aca gaa ctc gac cct ccc aga aac ctt cgt cca        2928
Asp Thr Lys Ala Gln Thr Glu Leu Asp Pro Pro Arg Asn Leu Arg Pro
            965                 970                 975 tct gct gta acg cag tct ggt ggc ata ttg acc tgg acg ccc cct tct        2976
Ser Ala Val Thr Gln Ser Gly Gly Ile Leu Thr Trp Thr Pro Pro Ser
        980                 985                 990 gct cag atc cac ggc tac att ctg act tac cag ttc cca gat ggc aca        3024
Ala Gln Ile His Gly Tyr Ile Leu Thr Tyr Gln Phe Pro Asp Gly Thr
    995                 1000                1005 gtt aag gag atg cag ctg gga cgg gaa gac cag agg ttt gcg ttg caa        3072
```

```
                Val Lys Glu Met Gln Leu Gly Arg Glu Asp Gln Arg Phe Ala Leu Gln
                    1010                1015                1020 ggc ctt gag caa ggc gcc acc tac cct gtc tcc ctt gtt gcc ttt aag         3120
Gly Leu Glu Gln Gly Ala Thr Tyr Pro Val Ser Leu Val Ala Phe Lys
1025                1030                1035                1040 ggt ggt cgc cgg agc aga aat gta tcc acc ctc tcc aca gtt ggt             3168
Gly Gly Arg Arg Ser Arg Asn Val Ser Thr Thr Leu Ser Thr Val Gly
                1045                1050                1055 gcc cgt ttc cca cac cct tcg gac tgc agt cag gtt cag cag aac agc         3216
Ala Arg Phe Pro His Pro Ser Asp Cys Ser Gln Val Gln Gln Asn Ser
            1060                1065                1070 aat gcc gcc agt ggt ctg tac acc atc tac ctg cat ggc gat gcc agc         3264
Asn Ala Ala Ser Gly Leu Tyr Thr Ile Tyr Leu His Gly Asp Ala Ser
        1075                1080                1085 cgg ccc ctg cag gtg tac tgt gac atg gaa acg gac gga ggt ggc tgg         3312
Arg Pro Leu Gln Val Tyr Cys Asp Met Glu Thr Asp Gly Gly Gly Trp
    1090                1095                1100 att gtc ttc cag agg cgg aac act ggg cag ctg gat ttc ttc aag cga         3360
Ile Val Phe Gln Arg Arg Asn Thr Gly Gln Leu Asp Phe Phe Lys Arg
1105                1110                1115                1120 tgg agg agc tat gtg gaa ggc ttt ggg gac ccc atg aag gag ttc tgg         3408
Trp Arg Ser Tyr Val Glu Gly Phe Gly Asp Pro Met Lys Glu Phe Trp
                1125                1130                1135 ctt gga ctt gac aag cta cac aac ctc acc acc ggc act cca gcg cgg         3456
Leu Gly Leu Asp Lys Leu His Asn Leu Thr Thr Gly Thr Pro Ala Arg
            1140                1145                1150 tat gag gtg aga gtg gat tta cag act gcc aat gaa tct gcc tat gct         3504
Tyr Glu Val Arg Val Asp Leu Gln Thr Ala Asn Glu Ser Ala Tyr Ala
        1155                1160                1165 ata tat gat ttc ttc caa gtg gcc tcc agc aag gag cgg tat aag ctg         3552
Ile Tyr Asp Phe Phe Gln Val Ala Ser Ser Lys Glu Arg Tyr Lys Leu
    1170                1175                1180 aca gtt ggg aaa tac aga ggc acg gca ggg gat gct ctt act tac cac         3600
Thr Val Gly Lys Tyr Arg Gly Thr Ala Gly Asp Ala Leu Thr Tyr His
1185                1190                1195                1200 aat gga tgg aag ttt aca act ttt gac aga gac aat gat atc gca ctc         3648
Asn Gly Trp Lys Phe Thr Thr Phe Asp Arg Asp Asn Asp Ile Ala Leu
                1205                1210                1215 agc aac tgt gcc ctg aca cat cat ggt ggc tgg tgg tat aag aac tgc         3696
Ser Asn Cys Ala Leu Thr His His Gly Gly Trp Trp Tyr Lys Asn Cys
            1220                1225                1230 cac ttg gcc aac cct aat ggc aga tat ggg gag acc aag cac agt gag         3744
His Leu Ala Asn Pro Asn Gly Arg Tyr Gly Glu Thr Lys His Ser Glu
        1235                1240                1245 ggg gtg aac tgg gag cct tgg aaa gga cat gaa ttc tcc att cct tac         3792
Gly Val Asn Trp Glu Pro Trp Lys Gly His Glu Phe Ser Ile Pro Tyr
    1250                1255                1260 gtg gag ttg aaa atc cgc cct cat ggc tac agc agg gag cct gtc ctg         3840
Val Glu Leu Lys Ile Arg Pro His Gly Tyr Ser Arg Glu Pro Val Leu
1265                1270                1275                1280 ggc aga aag aag cgg acg ctg aga gga agg ctg cga acg ttc tga             3885
Gly Arg Lys Lys Arg Thr Leu Arg Gly Arg Leu Arg Thr Phe *
                1285                1290

<210> SEQ ID NO 4
<211> LENGTH: 1294
<212> TYPE: PRT
<213> ORGANISM: Homo sapiens

<400> SEQUENCE: 4
```

```
Met Phe Arg Phe Pro Met Gly Leu Leu Leu Gly Ser Val Leu Leu Val
 1               5                  10                  15

Ala Ser Ala Pro Ala Thr Leu Glu Pro Pro Gly Cys Ser Asn Lys Glu
             20                  25                  30

Gln Gln Val Thr Val Ser His Thr Tyr Lys Ile Asp Val Pro Lys Ser
         35                  40                  45

Ala Leu Val Gln Val Asp Ala Asp Pro Gln Pro Leu Ser Asp Asp Gly
 50                  55                  60

Ala Ser Leu Leu Ala Leu Gly Glu Ala Arg Glu Gln Asn Ile Ile
 65                  70                  75                  80

Phe Arg His Asn Ile Arg Leu Gln Thr Pro Gln Lys Asp Cys Glu Leu
                 85                  90                  95

Ala Gly Ser Val Gln Asp Leu Leu Ala Arg Val Lys Lys Leu Glu Glu
             100                 105                 110

Glu Met Val Glu Met Lys Glu Gln Cys Ser Ala Gln Arg Cys Cys Gln
             115                 120                 125

Gly Val Thr Asp Leu Ser Arg His Cys Ser Gly His Gly Thr Phe Ser
         130                 135                 140

Leu Glu Thr Cys Ser Cys His Cys Glu Glu Gly Arg Glu Gly Pro Ala
145                 150                 155                 160

Cys Glu Arg Leu Ala Cys Pro Gly Ala Cys Ser Gly His Gly Arg Cys
                 165                 170                 175

Val Asp Gly Arg Cys Leu Cys His Glu Pro Tyr Val Gly Ala Asp Cys
             180                 185                 190

Gly Tyr Pro Ala Cys Pro Glu Asn Cys Ser Gly His Gly Glu Cys Val
         195                 200                 205

Arg Gly Val Cys Gln Cys His Glu Asp Phe Met Ser Glu Asp Cys Ser
210                 215                 220

Glu Lys Arg Cys Pro Gly Asp Cys Ser Gly His Gly Phe Cys Asp Thr
225                 230                 235                 240

Gly Glu Cys Tyr Cys Glu Gly Phe Thr Gly Leu Asp Cys Ala Gln
                 245                 250                 255

Val Val Thr Pro Gln Gly Leu Gln Leu Leu Lys Asn Thr Glu Asp Ser
             260                 265                 270

Leu Leu Val Ser Trp Glu Pro Ser Ser Gln Val Asp His Tyr Leu Leu
         275                 280                 285

Ser Tyr Tyr Pro Leu Gly Lys Glu Leu Ser Gly Lys Gln Ile Gln Val
290                 295                 300

Pro Lys Glu Gln His Ser Tyr Glu Ile Leu Gly Leu Pro Gly Thr
305                 310                 315                 320

Lys Tyr Ile Val Thr Leu Arg Asn Val Lys Asn Glu Val Ser Ser Ser
                 325                 330                 335

Pro Gln His Leu Leu Ala Thr Thr Asp Leu Ala Val Leu Gly Thr Ala
             340                 345                 350

Trp Val Thr Asp Glu Thr Glu Asn Ser Leu Asp Val Glu Trp Glu Asn
         355                 360                 365

Pro Ser Thr Glu Val Asp Tyr Tyr Lys Leu Arg Tyr Gly Pro Met Thr
370                 375                 380

Gly Gln Glu Val Ala Glu Val Thr Val Pro Lys Ser Ser Asp Pro Lys
385                 390                 395                 400

Ser Arg Tyr Asp Ile Thr Gly Leu His Pro Gly Thr Glu Tyr Lys Ile
                 405                 410                 415

Thr Val Val Pro Met Arg Gly Glu Leu Glu Gly Lys Pro Ile Leu Leu
```

```
                420             425             430
Asn Gly Arg Thr Glu Ile Asp Ser Pro Thr Asn Val Val Thr Asp Arg
            435                 440                 445

Val Thr Glu Asp Thr Ala Thr Val Ser Trp Asp Pro Val Gln Ala Val
    450                 455                 460

Ile Asp Lys Tyr Val Val Arg Tyr Thr Ser Ala Asp Gly Asp Thr Lys
465                 470                 475                 480

Glu Met Ala Val His Lys Asp Glu Ser Ser Thr Val Leu Thr Gly Leu
                    485                 490                 495

Lys Pro Gly Glu Ala Tyr Lys Val Tyr Val Trp Ala Glu Arg Gly Asn
                500                 505                 510

Gln Gly Ser Lys Lys Ala Asp Thr Asn Ala Leu Thr Glu Ile Asp Ser
            515                 520                 525

Pro Ala Asn Leu Val Thr Asp Arg Val Thr Glu Asn Thr Ala Thr Ile
            530                 535                 540

Ser Trp Asp Pro Val Gln Ala Thr Ile Asp Lys Tyr Val Val Arg Tyr
545                 550                 555                 560

Thr Ser Ala Asp Asp Gln Glu Thr Arg Glu Val Leu Val Gly Lys Glu
                565                 570                 575

Gln Ser Ser Thr Val Leu Thr Gly Leu Arg Pro Gly Val Glu Tyr Thr
                580                 585                 590

Val His Val Trp Ala Gln Lys Gly Asp Arg Glu Ser Lys Lys Ala Asp
            595                 600                 605

Thr Asn Ala Pro Thr Asp Ile Asp Ser Pro Lys Asn Leu Val Thr Asp
        610                 615                 620

Arg Val Thr Glu Asn Met Ala Thr Val Ser Trp Asp Pro Val Gln Ala
625                 630                 635                 640

Ala Ile Asp Lys Tyr Val Val Arg Tyr Thr Ser Ala Gly Gly Glu Thr
                    645                 650                 655

Arg Glu Val Pro Val Gly Lys Glu Gln Ser Ser Thr Val Leu Thr Gly
                660                 665                 670

Leu Arg Pro Gly Met Glu Tyr Met Val His Val Trp Ala Gln Lys Gly
            675                 680                 685

Asp Gln Glu Ser Lys Lys Ala Asp Thr Lys Ala Gln Thr Asp Ile Asp
        690                 695                 700

Ser Pro Gln Asn Leu Val Thr Asp Arg Val Thr Glu Asn Met Ala Thr
705                 710                 715                 720

Val Ser Trp Asp Pro Val Arg Ala Thr Ile Asp Arg Tyr Val Val Arg
                    725                 730                 735

Tyr Thr Ser Ala Lys Asp Gly Glu Thr Arg Glu Val Pro Val Gly Lys
                740                 745                 750

Glu Gln Ser Ser Thr Val Leu Thr Gly Leu Arg Pro Gly Val Glu Tyr
            755                 760                 765

Thr Val His Val Trp Ala Gln Lys Gly Ala Gln Glu Ser Lys Lys Ala
        770                 775                 780

Asp Thr Lys Ala Gln Thr Asp Ile Asp Ser Pro Gln Asn Leu Val Thr
785                 790                 795                 800

Asp Trp Val Thr Glu Asn Thr Ala Thr Val Ser Trp Asp Pro Val Gln
                    805                 810                 815

Ala Thr Ile Asp Arg Tyr Val Val His Tyr Thr Ser Ala Asn Gly Glu
                820                 825                 830

Thr Arg Glu Val Pro Val Gly Lys Glu Gln Ser Ser Thr Val Leu Thr
            835                 840                 845
```

-continued

```
Gly Leu Arg Pro Gly Met Glu Tyr Thr Val His Val Trp Ala Gln Lys
    850                 855                 860
Gly Asn Gln Glu Ser Lys Lys Ala Asp Thr Lys Ala Gln Thr Glu Ile
865                 870                 875                 880
Asp Gly Pro Lys Asn Leu Val Thr Asp Trp Val Thr Glu Asn Met Ala
                885                 890                 895
Thr Val Ser Trp Asp Pro Val Gln Ala Thr Ile Asp Lys Tyr Met Val
            900                 905                 910
Arg Tyr Thr Ser Ala Asp Gly Glu Thr Arg Glu Val Pro Val Gly Lys
        915                 920                 925
Glu His Ser Ser Thr Val Leu Thr Gly Leu Arg Pro Gly Met Glu Tyr
    930                 935                 940
Met Val His Val Trp Ala Gln Lys Gly Ala Gln Glu Ser Lys Lys Ala
945                 950                 955                 960
Asp Thr Lys Ala Gln Thr Glu Leu Asp Pro Pro Arg Asn Leu Arg Pro
                965                 970                 975
Ser Ala Val Thr Gln Ser Gly Gly Ile Leu Thr Trp Thr Pro Pro Ser
            980                 985                 990
Ala Gln Ile His Gly Tyr Ile Leu Thr Tyr Gln Phe Pro Asp Gly Thr
        995                 1000                1005
Val Lys Glu Met Gln Leu Gly Arg Glu Asp Gln Arg Phe Ala Leu Gln
    1010                1015                1020
Gly Leu Glu Gln Gly Ala Thr Tyr Pro Val Ser Leu Val Ala Phe Lys
1025                1030                1035                1040
Gly Gly Arg Arg Ser Arg Asn Val Ser Thr Thr Leu Ser Thr Val Gly
                1045                1050                1055
Ala Arg Phe Pro His Pro Ser Asp Cys Ser Gln Val Gln Gln Asn Ser
            1060                1065                1070
Asn Ala Ala Ser Gly Leu Tyr Thr Ile Tyr Leu His Gly Asp Ala Ser
        1075                1080                1085
Arg Pro Leu Gln Val Tyr Cys Asp Met Glu Thr Asp Gly Gly Gly Trp
    1090                1095                1100
Ile Val Phe Gln Arg Arg Asn Thr Gly Gln Leu Asp Phe Phe Lys Arg
1105                1110                1115                1120
Trp Arg Ser Tyr Val Glu Gly Phe Gly Asp Pro Met Lys Glu Phe Trp
                1125                1130                1135
Leu Gly Leu Asp Lys Leu His Asn Leu Thr Thr Gly Thr Pro Ala Arg
            1140                1145                1150
Tyr Glu Val Arg Val Asp Leu Gln Thr Ala Asn Glu Ser Ala Tyr Ala
        1155                1160                1165
Ile Tyr Asp Phe Phe Gln Val Ala Ser Ser Lys Glu Arg Tyr Lys Leu
    1170                1175                1180
Thr Val Gly Lys Tyr Arg Gly Thr Ala Gly Asp Ala Leu Thr Tyr His
1185                1190                1195                1200
Asn Gly Trp Lys Phe Thr Thr Phe Asp Arg Asp Asn Asp Ile Ala Leu
                1205                1210                1215
Ser Asn Cys Ala Leu Thr His His Gly Gly Trp Trp Tyr Lys Asn Cys
            1220                1225                1230
His Leu Ala Asn Pro Asn Gly Arg Tyr Gly Glu Thr Lys His Ser Glu
        1235                1240                1245
Gly Val Asn Trp Glu Pro Trp Lys Gly His Glu Phe Ser Ile Pro Tyr
    1250                1255                1260
```

```
Val Glu Leu Lys Ile Arg Pro His Gly Tyr Ser Arg Glu Pro Val Leu
1265                1270                1275                1280

Gly Arg Lys Lys Arg Thr Leu Arg Gly Arg Leu Arg Thr Phe
                1285                1290
```

```
<210> SEQ ID NO 5
<211> LENGTH: 25
<212> TYPE: DNA
<213> ORGANISM: Mus musculus
<220> FEATURE:
<221> NAME/KEY: primer_bind
<222> LOCATION: (1)...(25)
<223> OTHER INFORMATION: First polymerase chain reaction primer

<400> SEQUENCE: 5
tagcagccca cagcatctac ttgcc                                         25

<210> SEQ ID NO 6
<211> LENGTH: 27
<212> TYPE: DNA
<213> ORGANISM: Mus musculus
<220> FEATURE:
<221> NAME/KEY: primer_bind
<222> LOCATION: (1)...(27)
<223> OTHER INFORMATION: First polymerase chain reaction primer

<400> SEQUENCE: 6
attgctgttc tgctgaacct gactgca                                       27

<210> SEQ ID NO 7
<211> LENGTH: 34
<212> TYPE: DNA
<213> ORGANISM: Mus musculus
<220> FEATURE:
<221> NAME/KEY: primer_bind
<222> LOCATION: (1)...(34)
<223> OTHER INFORMATION: Second polymerase chain reaction primer

<400> SEQUENCE: 7
atggatccag aaattgacgg ccccaaaaac ctag                               34

<210> SEQ ID NO 8
<211> LENGTH: 33
<212> TYPE: DNA
<213> ORGANISM: Mus musculus
<220> FEATURE:
<221> NAME/KEY: primer_bind
<222> LOCATION: (1)...(33)
<223> OTHER INFORMATION: Second polymerase chain reaction primer

<400> SEQUENCE: 8
ataagcttgt ggagagggtg gtggatacat ttc                                33

<210> SEQ ID NO 9
<211> LENGTH: 24
<212> TYPE: DNA
<213> ORGANISM: Mus musculus
<220> FEATURE:
<221> NAME/KEY: primer_bind
<222> LOCATION: (1)...(24)
<223> OTHER INFORMATION: First PCR primer for sequencing 5' end

<400> SEQUENCE: 9
aggagatggt ggctgtattt tcgg                                          24

<210> SEQ ID NO 10
<211> LENGTH: 24
```

```
<210> SEQ ID NO 10
<211> LENGTH: 24
<212> TYPE: DNA
<213> ORGANISM: Mus musculus
<220> FEATURE:
<221> NAME/KEY: primer_bind
<222> LOCATION: (1)...(24)
<223> OTHER INFORMATION: First PCR primer for sequencing 5' end

<400> SEQUENCE: 10
agcctcttgc tgagtggaga tgcc                                           24

<210> SEQ ID NO 11
<211> LENGTH: 30
<212> TYPE: DNA
<213> ORGANISM: Mus musculus
<220> FEATURE:
<221> NAME/KEY: primer_bind
<222> LOCATION: (1)...(30)
<223> OTHER INFORMATION: Second PCR primer for sequencing 5' end

<400> SEQUENCE: 11
tagaattcgg tcacctgatt ggtcactagg                                     30

<210> SEQ ID NO 12
<211> LENGTH: 22
<212> TYPE: DNA
<213> ORGANISM: Mus musculus
<220> FEATURE:
<221> NAME/KEY: primer_bind
<222> LOCATION: (1)...(22)
<223> OTHER INFORMATION: Second PCR primer for sequencing 5' end

<400> SEQUENCE: 12
ttatgatgtg ccagattatg cc                                             22

<210> SEQ ID NO 13
<211> LENGTH: 26
<212> TYPE: DNA
<213> ORGANISM: Mus musculus
<220> FEATURE:
<221> NAME/KEY: primer_bind
<222> LOCATION: (1)...(26)
<223> OTHER INFORMATION: First PCR reaction for sequencing 3' end

<400> SEQUENCE: 13
ctcaaattga tggctacatt ttgacc                                         26

<210> SEQ ID NO 14
<211> LENGTH: 24
<212> TYPE: DNA
<213> ORGANISM: Mus musculus
<220> FEATURE:
<221> NAME/KEY: primer_bind
<222> LOCATION: (1)...(24)
<223> OTHER INFORMATION: First PCR primer for sequencing 3' end

<400> SEQUENCE: 14
aagccgacaa ccttgattgg agac                                           24

<210> SEQ ID NO 15
<211> LENGTH: 22
<212> TYPE: DNA
<213> ORGANISM: Mus musculus
<220> FEATURE:
<221> NAME/KEY: primer_bind
<222> LOCATION: (1)...(22)
<223> OTHER INFORMATION: Second PCR primer for sequencing 3' end

<400> SEQUENCE: 15
```

```
taccagttcc caaatggcac cg                                               22

<210> SEQ ID NO 16
<211> LENGTH: 21
<212> TYPE: DNA
<213> ORGANISM: Mus musculus
<220> FEATURE:
<221> NAME/KEY: primer_bind
<222> LOCATION: (1)...(21)
<223> OTHER INFORMATION: Second PCR primer for sequencing 3' end

<400> SEQUENCE: 16
aaacctctgg cgaagaagtc c                                                21

<210> SEQ ID NO 17
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: hTNW1

<400> SEQUENCE: 17
catcctggag ggtctgctcc                                                  20

<210> SEQ ID NO 18
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: hTNW2

<400> SEQUENCE: 18
gggcattggt gtcagctttc                                                  20

<210> SEQ ID NO 19
<211> LENGTH: 28
<212> TYPE: DNA
<213> ORGANISM: Homo sapiens
<220> FEATURE:
<221> NAME/KEY: primer_bind
<222> LOCATION: (1)...(28)
<223> OTHER INFORMATION: hTNW3

<400> SEQUENCE: 19
gactcgagct ttccaaggat gagtctcc                                         28

<210> SEQ ID NO 20
<211> LENGTH: 26
<212> TYPE: DNA
<213> ORGANISM: Homo sapiens
<220> FEATURE:
<221> NAME/KEY: primer_bind
<222> LOCATION: (1)...(26)
<223> OTHER INFORMATION: hTNW4

<400> SEQUENCE: 20
gaggatcccc tggttgcccc tttcag                                           26

<210> SEQ ID NO 21
<211> LENGTH: 20
<212> TYPE: DNA
<213> ORGANISM: Homo sapiens
<220> FEATURE:
<221> NAME/KEY: primer_bind
```

<222> LOCATION: (1)...(20)
<223> OTHER INFORMATION: hTNW5

<400> SEQUENCE: 21
gcgctacact tctgctgatg                    20

<210> SEQ ID NO 22
<211> LENGTH: 18
<212> TYPE: DNA
<213> ORGANISM: Homo sapiens
<220> FEATURE:
<221> NAME/KEY: primer_bind
<222> LOCATION: (1)...(18)
<223> OTHER INFORMATION: hTNW6

<400> SEQUENCE: 22
ctgtggagag ggtggtgg                      18

<210> SEQ ID NO 23
<211> LENGTH: 27
<212> TYPE: DNA
<213> ORGANISM: Homo sapiens
<220> FEATURE:
<221> NAME/KEY: primer_bind
<222> LOCATION: (1)...(27)
<223> OTHER INFORMATION: hTNW7

<400> SEQUENCE: 23
gactcgagtg cacaaggatg agagcag            27

<210> SEQ ID NO 24
<211> LENGTH: 28
<212> TYPE: DNA
<213> ORGANISM: Homo sapiens
<220> FEATURE:
<221> NAME/KEY: primer_bind
<222> LOCATION: (1)...(28)
<223> OTHER INFORMATION: hTNW8

<400> SEQUENCE: 24
gaggatccac ccttaaaggc aacaaggg           28

<210> SEQ ID NO 25
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: hTNW9

<400> SEQUENCE: 25
cgcagtctgg tggcatattg                    20

<210> SEQ ID NO 26
<211> LENGTH: 19
<212> TYPE: DNA
<213> ORGANISM: Homo sapiens
<220> FEATURE:
<221> NAME/KEY: primer_bind
<222> LOCATION: (1)...(19)
<223> OTHER INFORMATION: hTNW10

<400> SEQUENCE: 26
catgatttgt tctgcgggc                     19

<210> SEQ ID NO 27

```
<211> LENGTH: 28
<212> TYPE: DNA
<213> ORGANISM: Homo sapiens
<220> FEATURE:
<221> NAME/KEY: primer_bind
<222> LOCATION: (1)...(28)
<223> OTHER INFORMATION: hTNW11

<400> SEQUENCE: 27
gactcgagcg gctacattct gacttacc                                              28

<210> SEQ ID NO 28
<211> LENGTH: 29
<212> TYPE: DNA
<213> ORGANISM: Homo sapiens
<220> FEATURE:
<221> NAME/KEY: primer_bind
<222> LOCATION: (1)...(29)
<223> OTHER INFORMATION: hTNW12

<400> SEQUENCE: 28
gaggatcctc agtgatggtg atggtgatg                                             29
```